US008211462B2

(12) United States Patent
Breitenbach et al.

(10) Patent No.: US 8,211,462 B2
(45) Date of Patent: *Jul. 3, 2012

(54) HOT-MELT TTS FOR ADMINISTERING ROTIGOTINE

(75) Inventors: Armin Breitenbach, Monheim (DE); Hans-Michael Wolff, Monheim (DE)

(73) Assignee: UCB Pharma GmbH, Monheim (DE)

(*) Notice: Subject to any disclaimer, the term of this patent is extended or adjusted under 35 U.S.C. 154(b) by 1165 days.

This patent is subject to a terminal disclaimer.

(21) Appl. No.: 10/630,633

(22) Filed: Jul. 29, 2003

(65) Prior Publication Data

US 2004/0137045 A1 Jul. 15, 2004

Related U.S. Application Data

(60) Provisional application No. 60/453,498, filed on Mar. 11, 2003.

(30) Foreign Application Priority Data

Jul. 30, 2002 (DE) .................................. 102 34 673

(51) Int. Cl.
*A61K 9/70* (2006.01)
*A61L 15/00* (2006.01)

(52) U.S. Cl. ......................... 424/449; 424/443; 424/445

(58) Field of Classification Search ........................ None
See application file for complete search history.

(56) References Cited

U.S. PATENT DOCUMENTS 4,144,317 A 3/1979 Higuchi et al. ................. 424/21
4,863,970 A 9/1989 Patel et al. .................... 514/772
4,880,633 A * 11/1989 Loper et al. ................... 424/449
4,915,950 A 4/1990 Miranda et al. ............... 424/448
4,973,468 A 11/1990 Chiang et al. ................. 424/449
5,043,482 A 8/1991 Maignan et al. .............. 568/734
5,069,909 A 12/1991 Sharma et al. ................ 424/449
5,091,186 A 2/1992 Miranda et al. ............... 424/448
5,124,157 A 6/1992 Colley et al. .................. 424/448
5,147,916 A 9/1992 Sweet ........................... 524/266
5,177,112 A 1/1993 Horn .............................. 514/65
5,225,198 A 7/1993 Sharma et al. ................ 424/443
5,234,690 A 8/1993 Chiang et al. ................. 424/448
5,246,997 A 9/1993 Sweet ........................... 524/266
5,252,334 A 10/1993 Chiang et al. ................. 424/448
5,252,335 A 10/1993 Chiang ........................ 424/449
5,271,940 A 12/1993 Cleary et al. .................. 424/448
5,273,755 A 12/1993 Venktrama et al. ........... 424/448
5,273,756 A 12/1993 Fallon et al. .................. 424/448
5,273,757 A 12/1993 Jaeger et al. .................. 424/448
5,308,625 A 5/1994 Wong et al. .................. 424/449
5,382,596 A 1/1995 Sleevi et al. .................. 514/459
5,393,529 A 2/1995 Hoffmann et al. ............ 424/445
5,456,745 A 10/1995 Roreger et al. ............... 106/128
5,527,536 A 6/1996 Merkle et al. ................. 424/448
5,554,381 A 9/1996 Roos et al. ................... 424/449
5,559,165 A 9/1996 Paul ............................. 523/111
5,601,839 A 2/1997 Quan et al. .................... 424/448
RE35,474 E 3/1997 Woodard et al. .............. 424/448
5,658,975 A 8/1997 Ulman et al. ................. 524/266
5,670,164 A 9/1997 Meconi et al. ................ 424/448
5,688,524 A 11/1997 Hsu et al. ...................... 424/449
5,733,571 A 3/1998 Sackler ......................... 424/499
5,771,890 A 6/1998 Tamada ........................ 128/635
5,807,570 A * 9/1998 Chen et al. .................... 424/449
5,834,010 A 11/1998 Quan et al. .................... 424/448
5,840,336 A 11/1998 Hsu et al. ...................... 424/484
5,843,472 A 12/1998 Ma et al. ....................... 427/449
5,876,746 A 3/1999 Jona et al. ..................... 424/449
5,879,701 A 3/1999 Audett et al. ................. 424/448
5,891,461 A 4/1999 Jona et al. ..................... 424/449
5,902,603 A 5/1999 Chen et al. .................... 424/449
5,906,830 A 5/1999 Farinas et al. ................ 424/448
5,980,932 A 11/1999 Chiang et al.
6,024,974 A 2/2000 Li ................................. 424/448
6,024,976 A 2/2000 Miranda et al. .............. 424/449
6,063,398 A 5/2000 Gueret .......................... 424/443
RE36,754 E * 6/2000 Noel ............................. 424/449
6,218,421 B1 4/2001 King ............................. 514/421
6,316,022 B1 11/2001 Mantelle et al. .............. 424/448
6,372,920 B1 4/2002 Minaskanian et al. .......... 549/75
6,393,318 B1 5/2002 Conn et al. ...................... 604/20
6,398,562 B1 6/2002 Butler et al. ..................... 439/91
6,465,004 B1 10/2002 Rossi-Montero et al. .... 424/448

(Continued)

FOREIGN PATENT DOCUMENTS

CA 2 532 804 2/2005

(Continued)

OTHER PUBLICATIONS

Metman et al., "Continuous Transdermal Dopaminergi Stimulation in Advanced Parkinson's Disease", Clinical Neuropharmacology 24(3):163-169, May/Jun. 2001.*

Krishna et al. "A Stability indicating of Rotigotine in Bulk Drugs by HPLC Assay method" Research Journal of Pharmaceutical, Biological and Chemical Sciences; pp. 848-857; 2010.*

Tanojo et al., "New design of flow-through permeation cell for studying in vitro permeation studies across biological membranes", *J. Controlled Release*, 1997, 45:41-47.

Van der Weide, et al. (1988) "The enantiomers of the D-2 dopamine receptor agonist N-0437 discriminate between pre- and postsynaptic dopamine receptors." Eur J Pharmacol 146:319-326.

(Continued)

*Primary Examiner* — Susan Tran
(74) *Attorney, Agent, or Firm* — Harness, Dickey & Pierce, P.L.C.

(57) ABSTRACT

This patent application relates to a transdermal therapeutic system (TTS) that comprises a Rotigotine-containing cement layer, characterized in that the cement layer contains a hot-meltable adhesive in which Rotigotine as the active substance is dispersed and partly or completely dissolved.

The patent application further relates to the use of Rotigotine in the production of the cement layer of a TTS by a hot-melt method.

25 Claims, 15 Drawing Sheets

U.S. PATENT DOCUMENTS

| | | | | |
|---|---|---|---|---|
| 6,620,429 | B1 | 9/2003 | Müller | 424/449 |
| 6,685,959 | B1 | 2/2004 | Moreau et al. | 424/449 |
| 6,687,522 | B2 | 2/2004 | Tamada | 600/347 |
| 6,699,498 | B1 | 3/2004 | Müller | 424/449 |
| 6,884,434 | B1 | 4/2005 | Muller et al. | 424/487 |
| 6,899,894 | B1 | 5/2005 | Klein et al. | 424/448 |
| 7,309,497 | B2 | 12/2007 | Rimpler et al. | 424/422 |
| 7,413,747 | B2 | 8/2008 | Mueller et al. | 424/448 |
| 2002/0110585 | A1 | 8/2002 | Godbey et al. | 424/449 |
| 2003/0026830 | A1 | 2/2003 | Lauterback et al. | 424/449 |
| 2003/0027793 | A1 | 2/2003 | Lauterback et al. | 514/63 |
| 2003/0166709 | A1 | 9/2003 | Rimpler et al. | 514/447 |
| 2004/0034083 | A1 | 2/2004 | Stephenson et al. | 514/406 |
| 2004/0048779 | A1 * | 3/2004 | Schollmayer | 514/2 |
| 2004/0057985 | A1 | 3/2004 | Bracht | |
| 2004/0081683 | A1 | 4/2004 | Schacht et al. | 424/449 |
| 2004/0110673 | A1 | 6/2004 | Steinkasserer et al. | 514/12 |
| 2004/0116537 | A1 | 6/2004 | Li et al. | 514/663 |
| 2004/0137045 | A1 | 7/2004 | Breitenbach et al. | 424/449 |
| 2004/0209861 | A1 | 10/2004 | Benavides et al. | 514/210.01 |
| 2005/0033065 | A1 | 2/2005 | Mueller et al. | 549/449 |
| 2005/0048104 | A1 * | 3/2005 | Venkatraman et al. | 424/449 |
| 2005/0079206 | A1 | 4/2005 | Schacht et al. | 424/449 |
| 2005/0136101 | A1 | 6/2005 | Berthold | 424/448 |
| 2005/0175678 | A1 | 8/2005 | Breitenbach | 424/449 |
| 2005/0175680 | A1 | 8/2005 | Morgan et al. | 424/448 |
| 2005/0197385 | A1 | 9/2005 | Scheller et al. | 514/438 |
| 2005/0222691 | A1 | 10/2005 | Glas et al. | 424/448 |
| 2005/0260254 | A1 | 11/2005 | Breitenbach et al. | 424/449 |
| 2006/0263419 | A1 | 11/2006 | Wolff | 424/448 |
| 2007/0072917 | A1 | 3/2007 | Scheller et al. | 514/357 |
| 2007/0093546 | A1 | 4/2007 | Scheller et al. | 514/447 |
| 2007/0191308 | A1 | 8/2007 | Kramer | 514/60 |
| 2007/0191470 | A1 | 8/2007 | Scheller | 514/438 |
| 2007/0197480 | A1 | 8/2007 | Scheller et al. | 514/114 |
| 2008/0008748 | A1 | 1/2008 | Beyreuther et al. | 424/449 |
| 2008/0138389 | A1 | 6/2008 | Muller et al. | 424/448 |
| 2008/0146622 | A1 | 6/2008 | Scheller | 514/357 |
| 2008/0274061 | A1 | 11/2008 | Schollmayer et al. | 424/45 |
| 2009/0143460 | A1 | 6/2009 | Wolff et al. | 514/438 |

FOREIGN PATENT DOCUMENTS

| | | |
|---|---|---|
| CA | 2 532 859 | 2/2005 |
| CA | 2 547 820 | 6/2005 |
| CA | 2 546 797 | 7/2005 |
| EP | 0 360 467 | 3/1990 |
| EP | 0 180 377 | 1/1991 |
| EP | 0 524 775 | 1/1993 |
| EP | 0 663 431 | 7/1995 |
| EP | 0663431 A2 * | 7/1995 |
| EP | 0 835 136 | 12/1996 |
| WO | WO 93/07842 | 4/1993 |
| WO | WO 93/14727 | 8/1993 |
| WO | WO 93/16073 | 8/1993 |
| WO | WO 94/04109 | 3/1994 |
| WO | WO 94/07468 | 4/1994 |
| WO | WO 95/00122 | 1/1995 |
| WO | WO 95/01767 | 1/1995 |
| WO | WO 95/05137 | 2/1995 |
| WO | WO 95/05138 | 2/1995 |
| WO | WO 95/24776 | 9/1995 |
| WO | WO 96/39136 | 12/1995 |
| WO | WO 96/00110 | 1/1996 |
| WO | WO 96/22083 | 7/1996 |
| WO | WO 96/22084 | 7/1996 |
| WO | WO 96/40087 | 12/1996 |
| WO | WO 97/09971 | 3/1997 |
| WO | WO 97/29735 | 8/1997 |

OTHER PUBLICATIONS

Office Action dated May 28, 2008 for U.S. Appl. No. 10/523,908.

Office Action dated Jul. 21, 2009 for U.S. Appl. No. 10/523,908.

Office Action dated Dec. 9, 2009 for U.S. Appl. No. 10/523,908.

The Merck Index http://www.medicinescomplete.com/mc/merck/2010/10253.htm (Printed Aug. 18, 2011).

Krishna, P., et al.,(2010) "A stability indicating of Rotigotine in bulk drugs by HPLC assay method" Research Journal of Pharmaceutical, Biological and Chemical Sciences, ISSN:0975-8575; pp. 848-857.

Organic Chemistry Reactions http://www.organic-chemistry.org/namedreactions/cope-elimination.shtm.(Printed Aug. 24, 2011).

Blindauer (2003) Arch. Neurol. 60(12): 1721-1728.

Chiang et al. (1995) Proc. Int. Symp. Controlled Release Bioact. Mater. 22, 710-711.

Hsu et al. (1992) Cygnus Therapeutic Systems Project Report N-0923, 2-19.

Levien et al. (2005) Advances in Pharmacy 3(1): 62-92.

LeWitt et al. (2007) Neurology 68, 1262-1267.

Löschmann et al. (1989) Eur. J. Pharmacol. 166: 373-380.

Pfister (1988) Drug and Cosmetic Ind. (Oct): 44-52.

Pfister (1989) Pharm. Tech. (March): 126-138.

Pfister and Hsieh (1990) Pharm. Tech. (Sept): 132-140.

Pfister and Hsieh (1990) Pharm. Tech. (Oct): 54-60.

Pfister et al. (1991) Chemistry in Britain (Jan): 43-46.

Pfister et al. (1992) Pharm. Tech. (Jan): 42-58 and 83.

Roy et al. (1996) J. Pharn. Science 85(5): 491-495.

Thomas et al. (1991) S.T.P. Pharma Sci 1(1): 38-46.

den Daas et al., *Naunyn-Schmiedegerg's Pharmacol.*,1990, 342:655-659.

European Public Assessment Report of the European Medicines Agency (EMEA, 2006) for Neupro®transdermal rotigotine (www.emea.europa.eu/humandocs/PDFs/EPAR/neupro/062606en6.pdf).

Jankovic & Tolosa, *Parkinson's Disease and Movement Disorders*, 5th ed., Philadelphia: Lippincott, pg. 121-122, 2006.

Swart et al, *Intematl. J. of Pharmaceutrics*, 1992, 88:165-170.

* cited by examiner

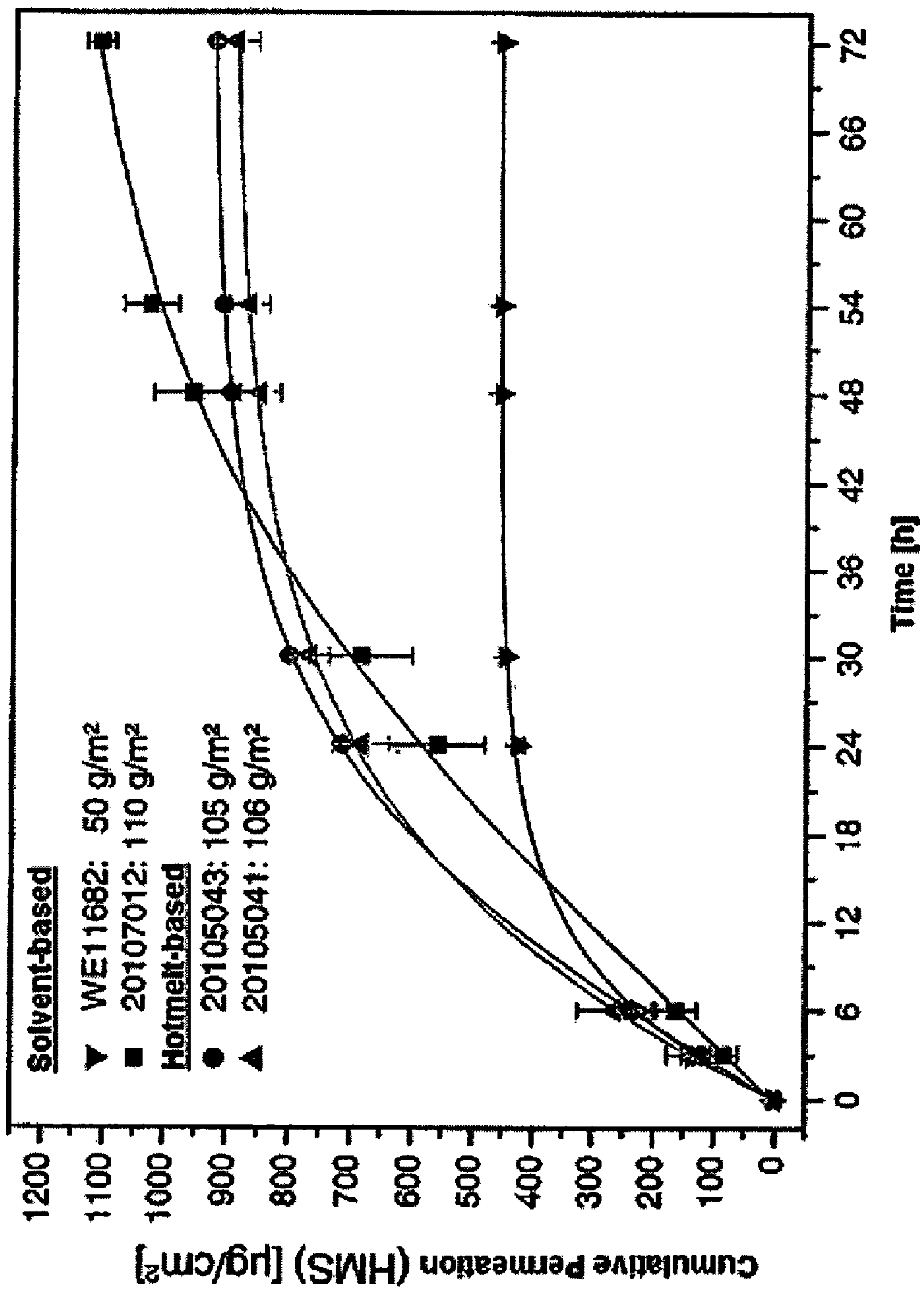
Figure 1a: Release through murine skin (HMS) from TTS containing 9% (w/w) Rotigotine

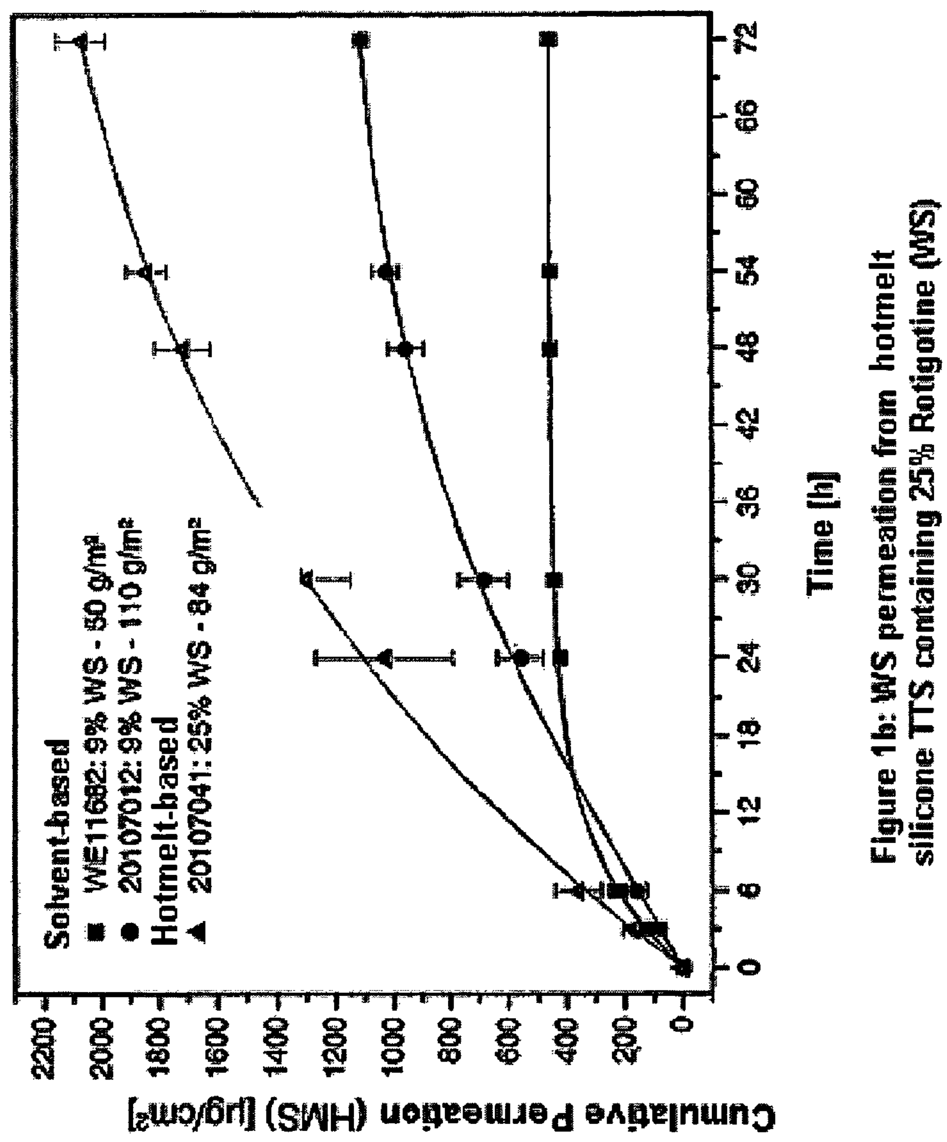
Figure 1b: WS permeation from hotmelt silicone TTS containing 25% Rotigotine (WS)

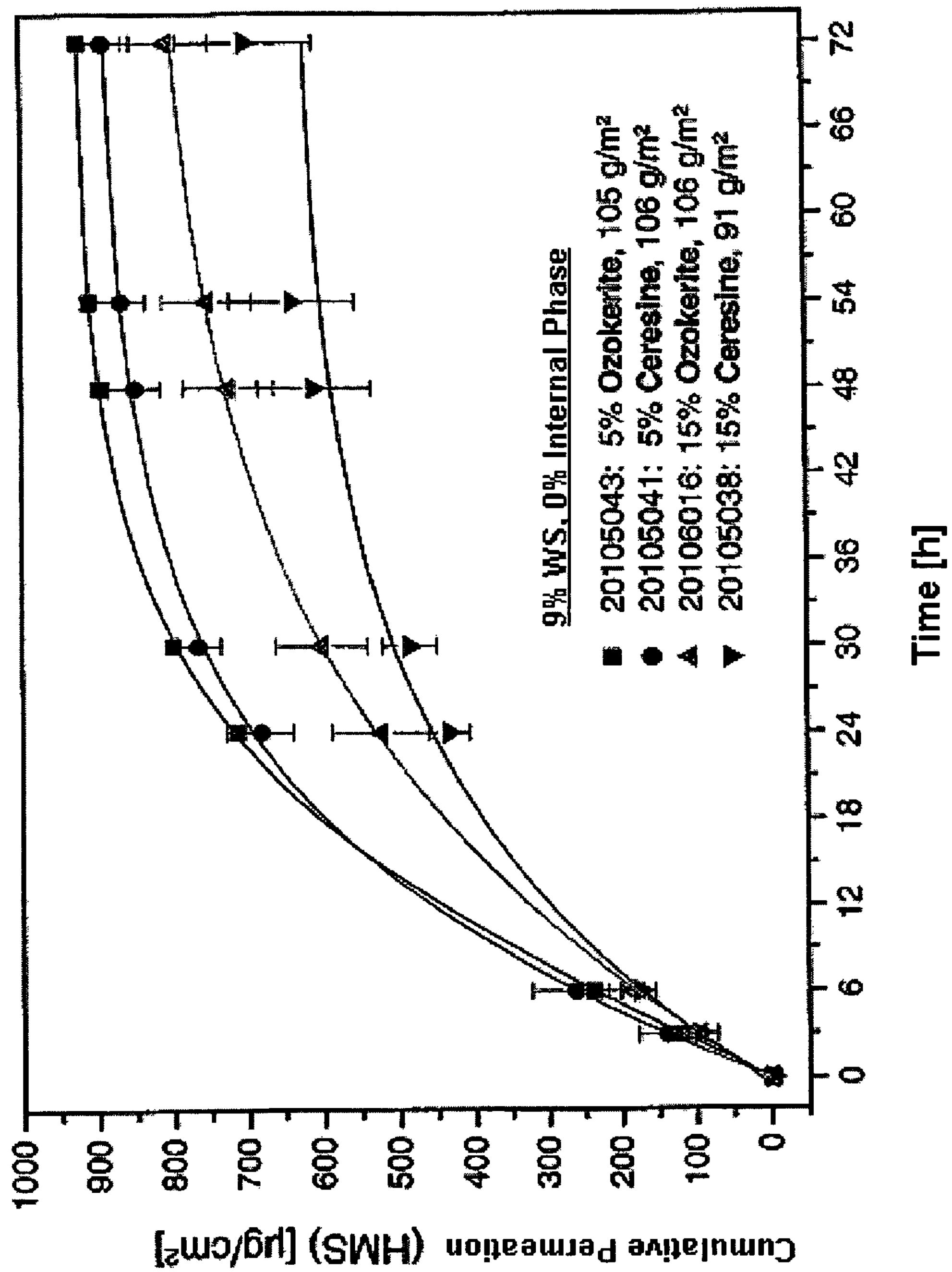
Figure 2: Effect of the wax content on Rotigotine (WS) permeation

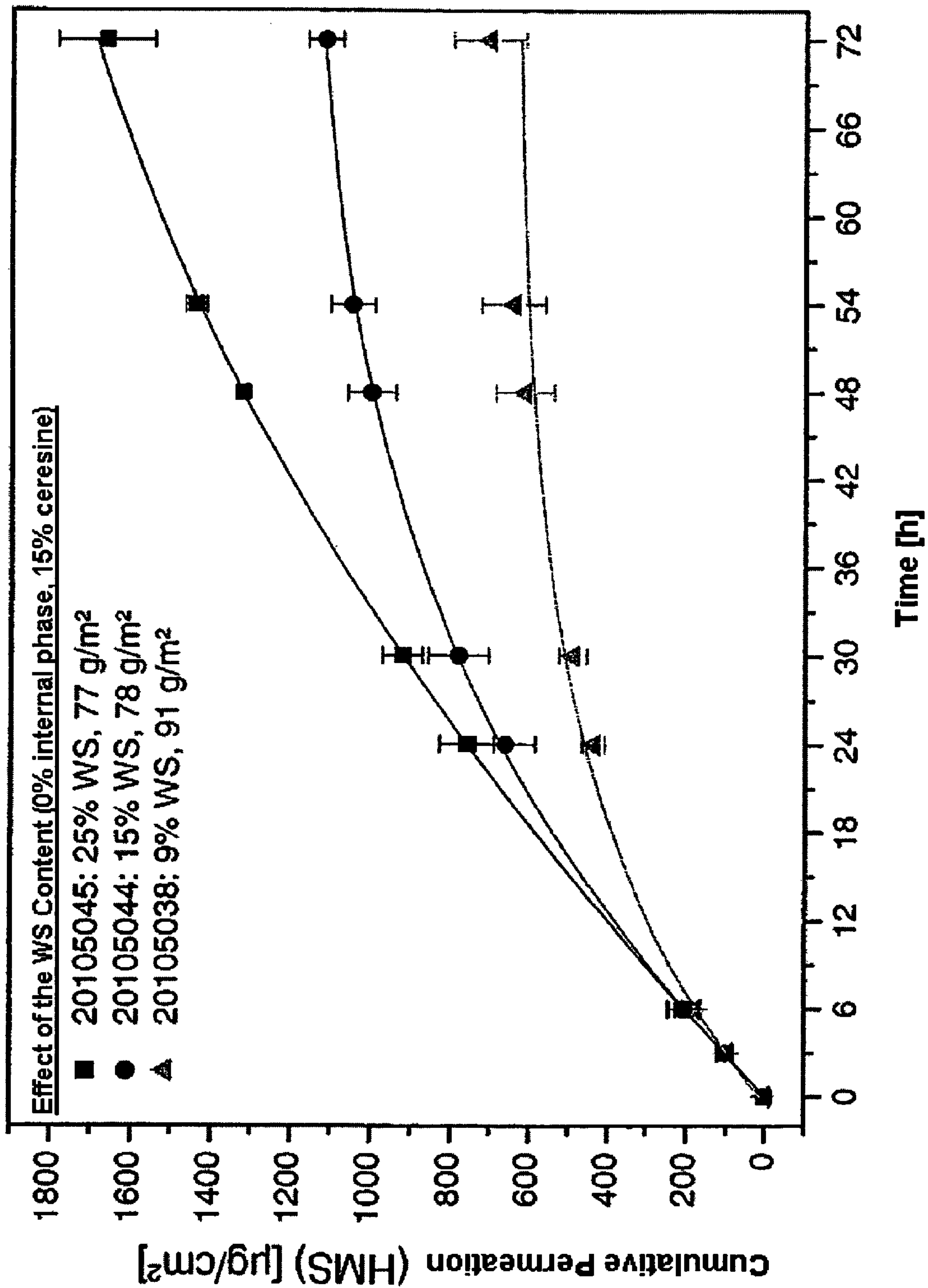
Figure 3a: Effect of the charge level on Rotigotine permeation

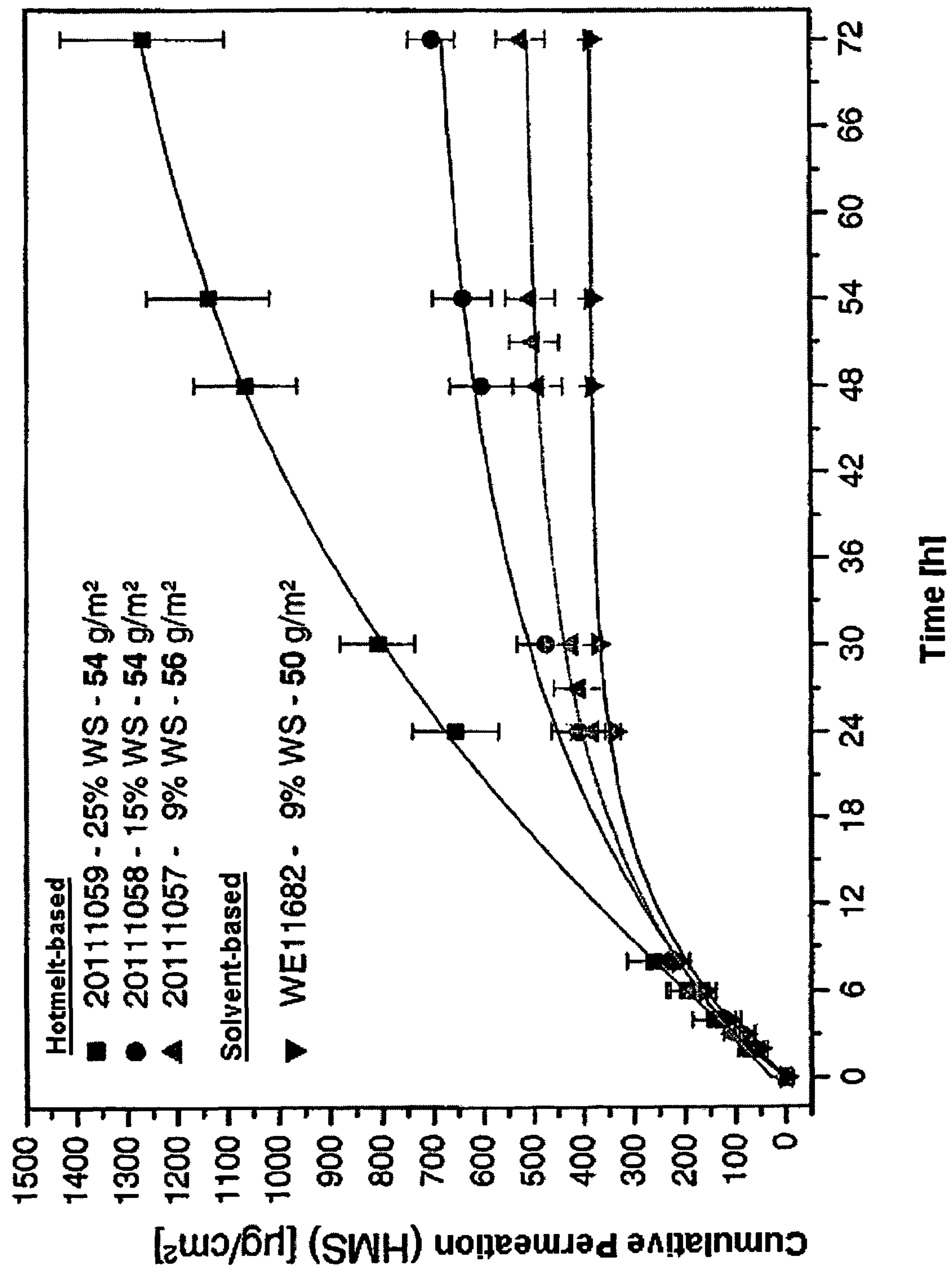
Figure 3b: Effect of the Rotigotine charge level on Rotigotine permeation

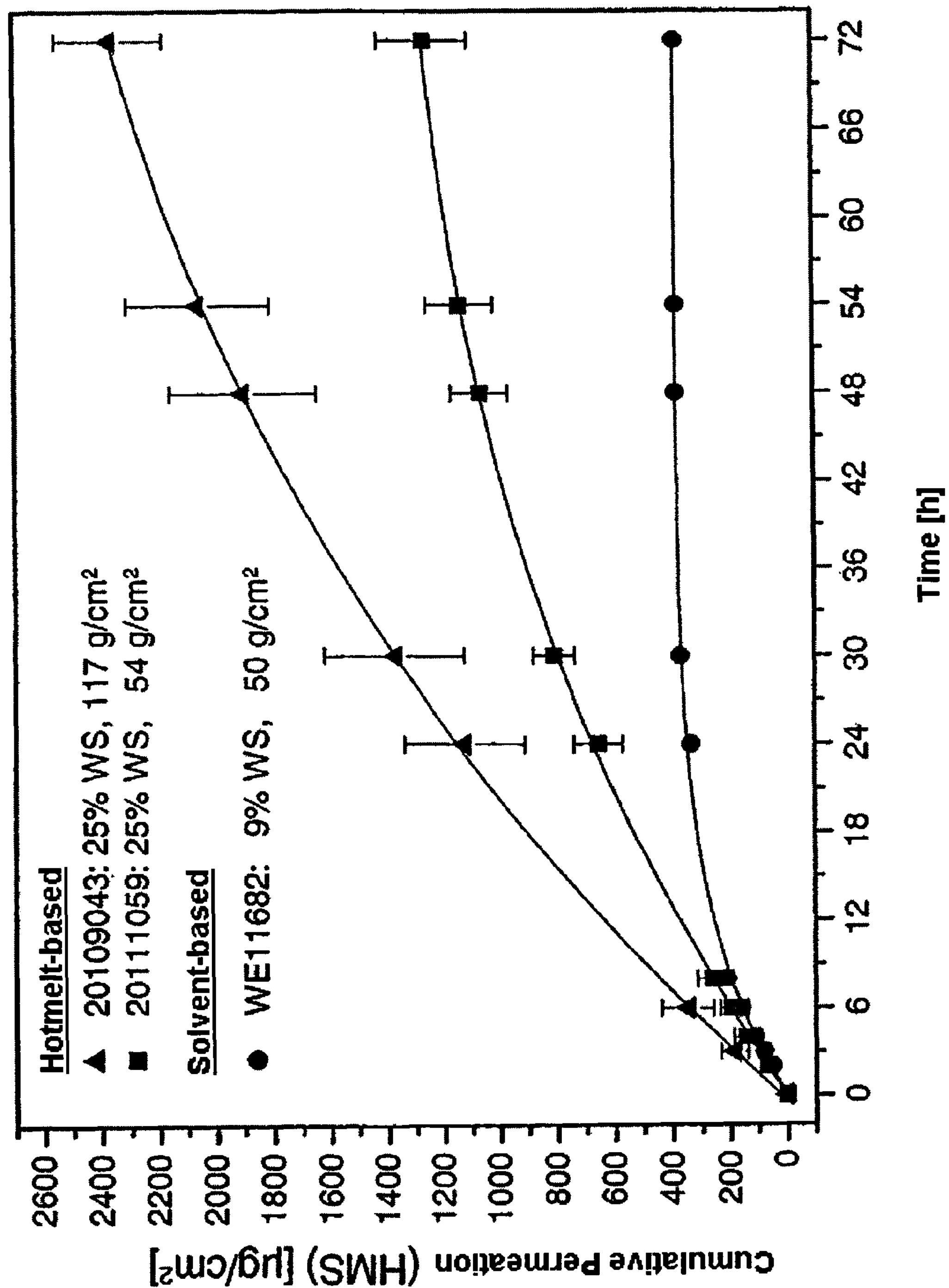
Figure 4: Effect of the matrix weight on Rotigotine permeation

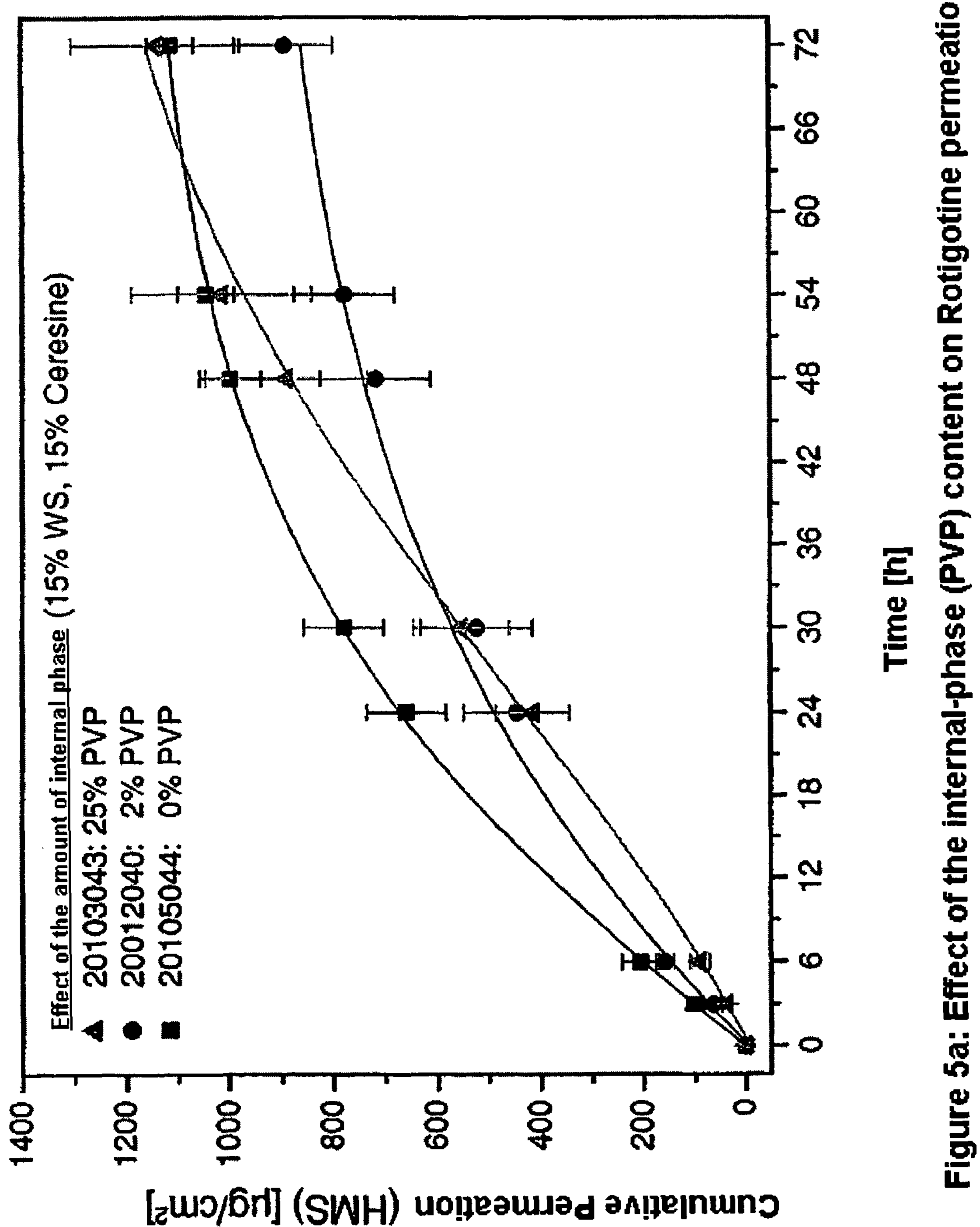
Figure 5a: Effect of the internal-phase (PVP) content on Rotigotine permeation

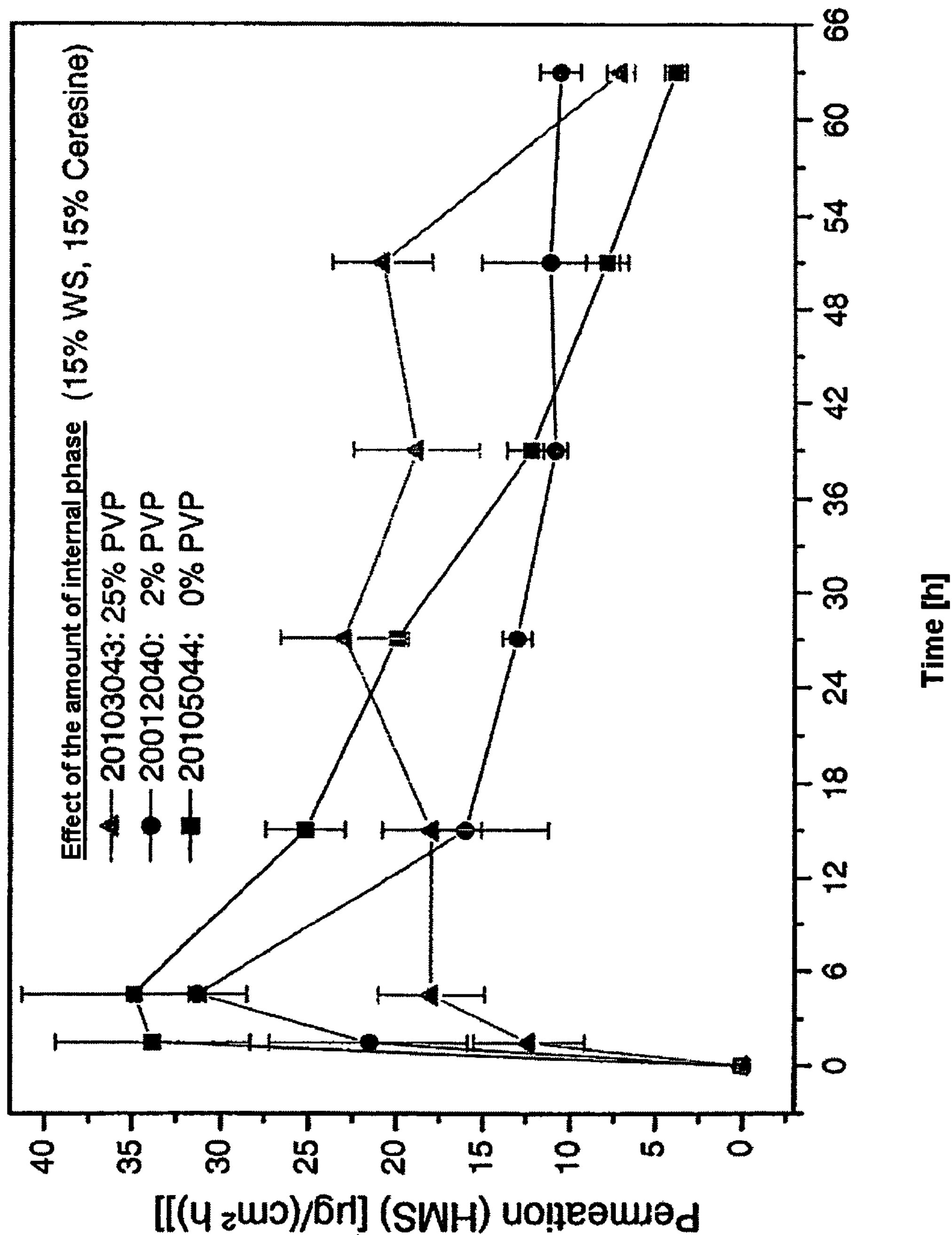
Figure 5b: Effect of the internal-phase (PVP) content on Rotigotine permeation

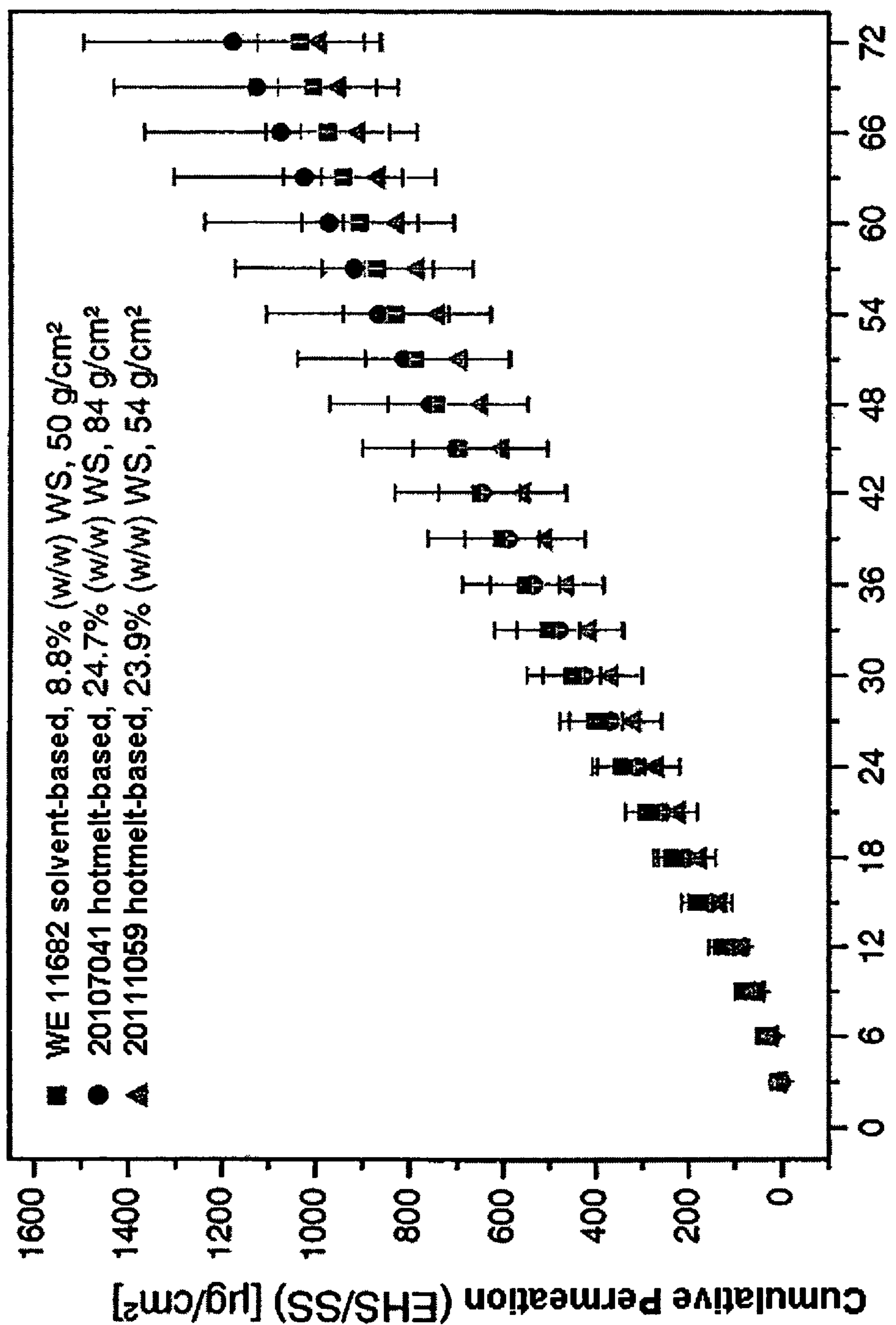
Figure 6a: Comparison of the cumulative Rotigotine permeation through human skin

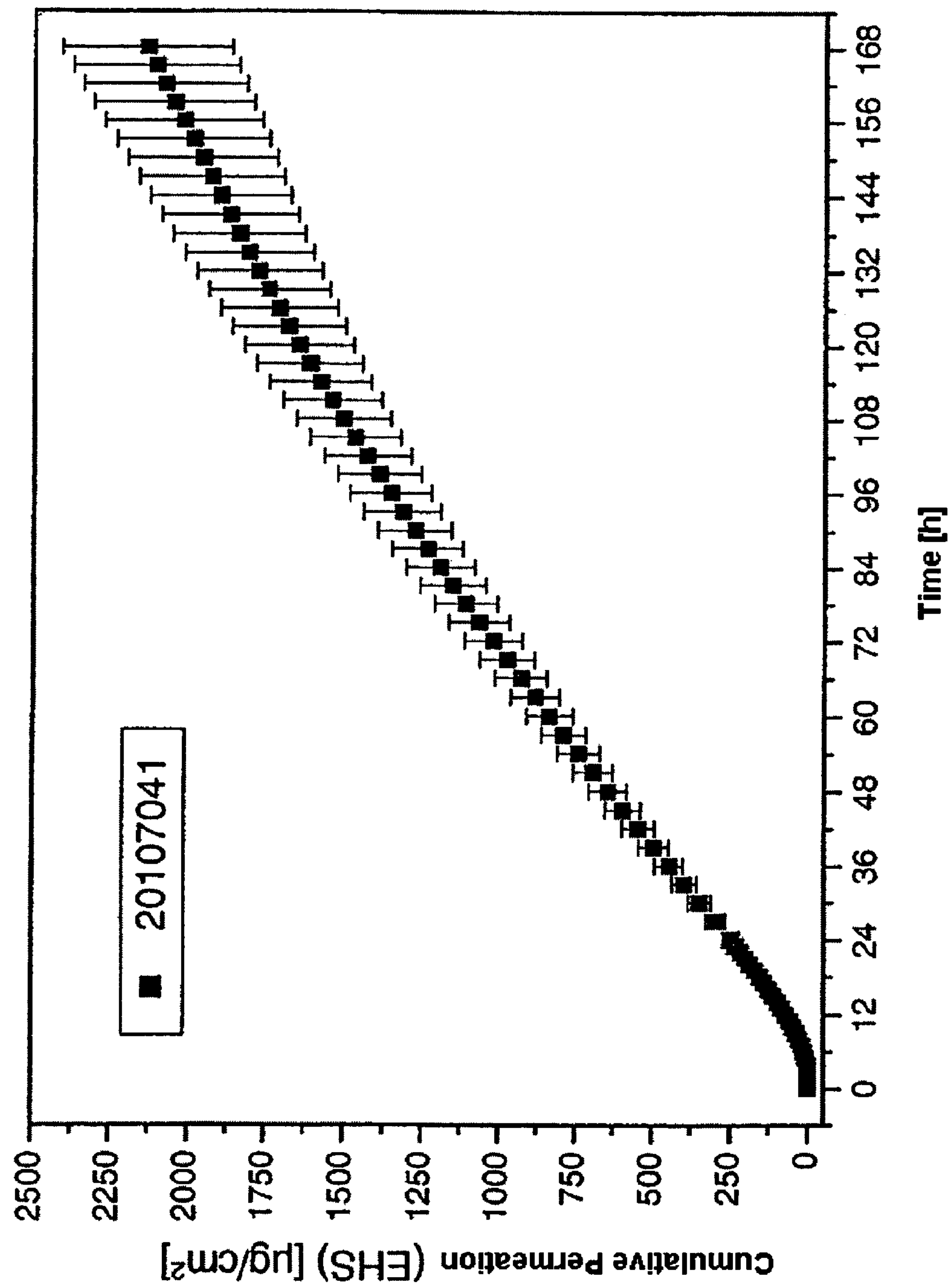
Figure 6b: Permeation of Rotigotine from a silicone-based hotmelt patch (25% weight % Rotigotine) through human skin

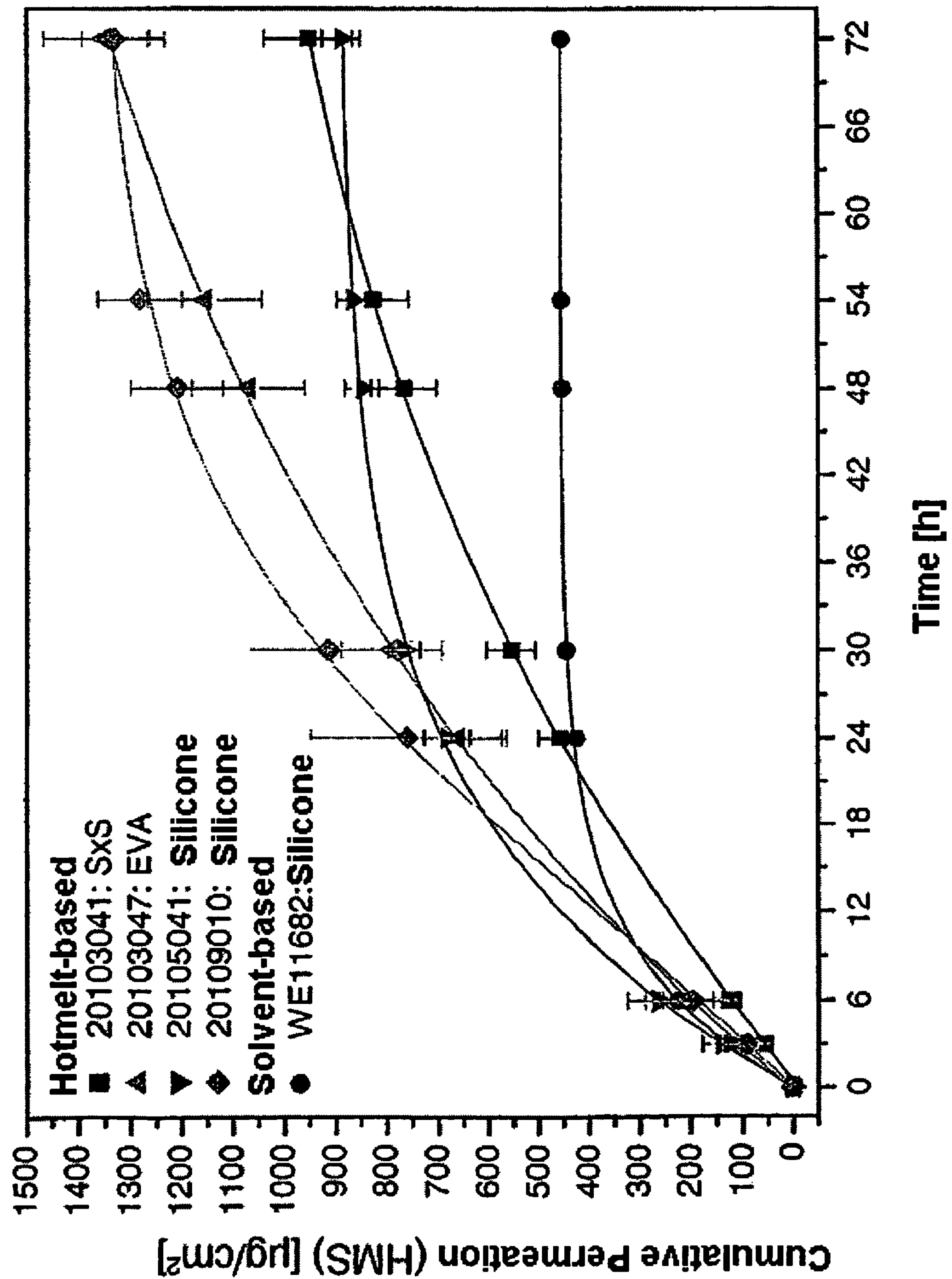
Figure 7: Rotigotine permeation from TTSs based on different hot-melt cements

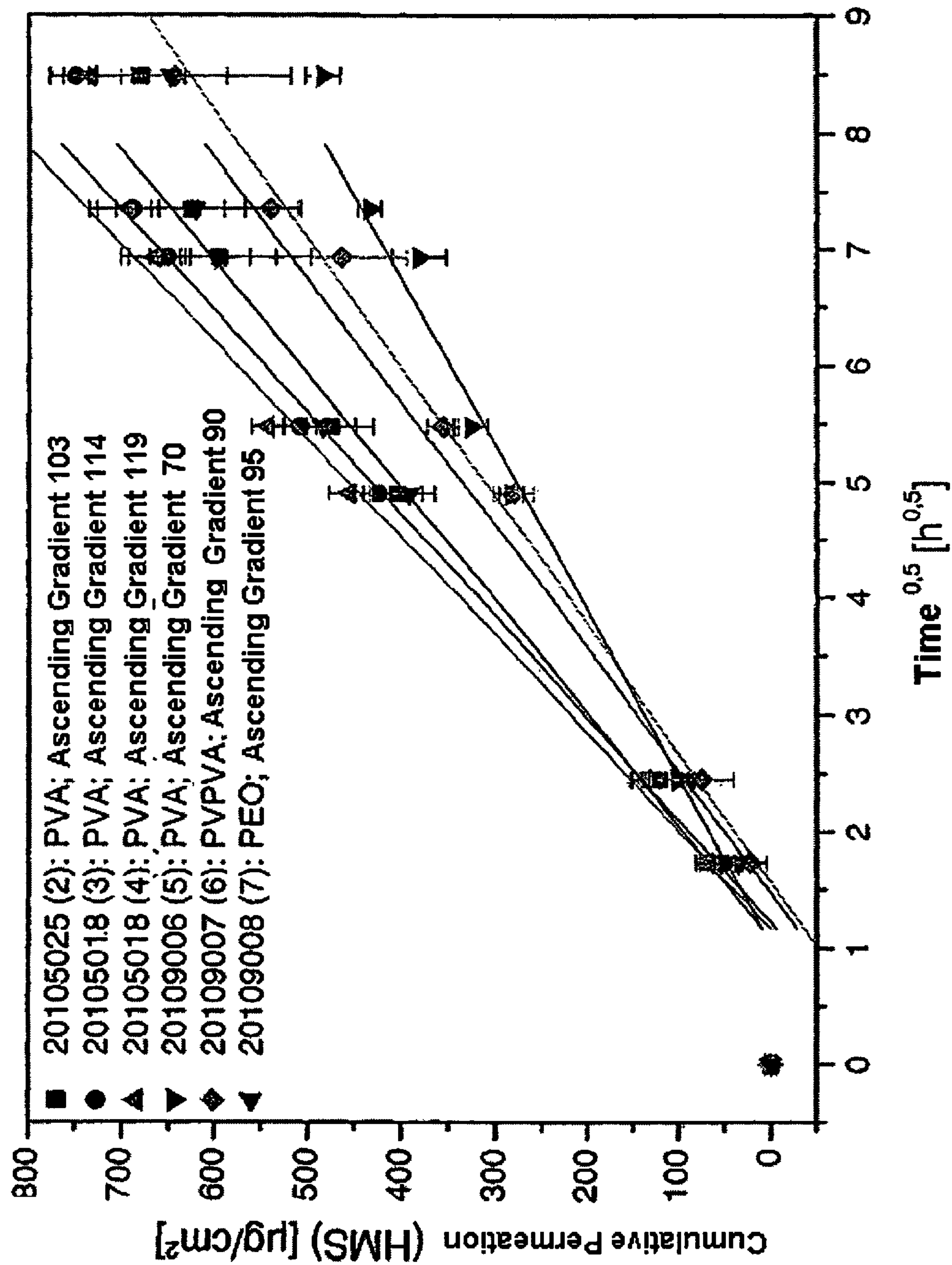
Figure 8: Rotigotine permeation from hot-melt silicone TTSs with different internal phases

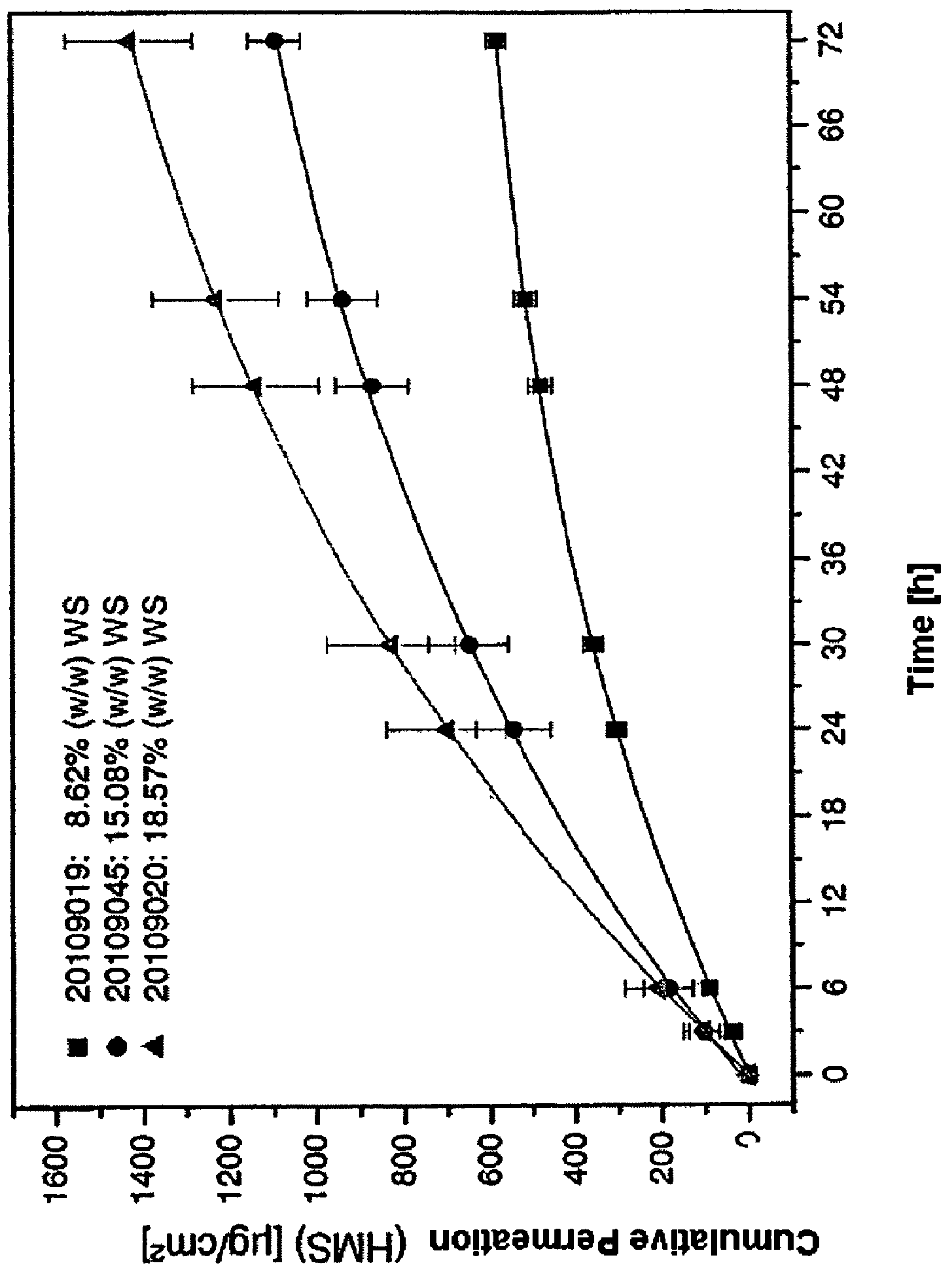
Figure 9: Rotigotine permeation from hot-melt EVA TTS through murine skin

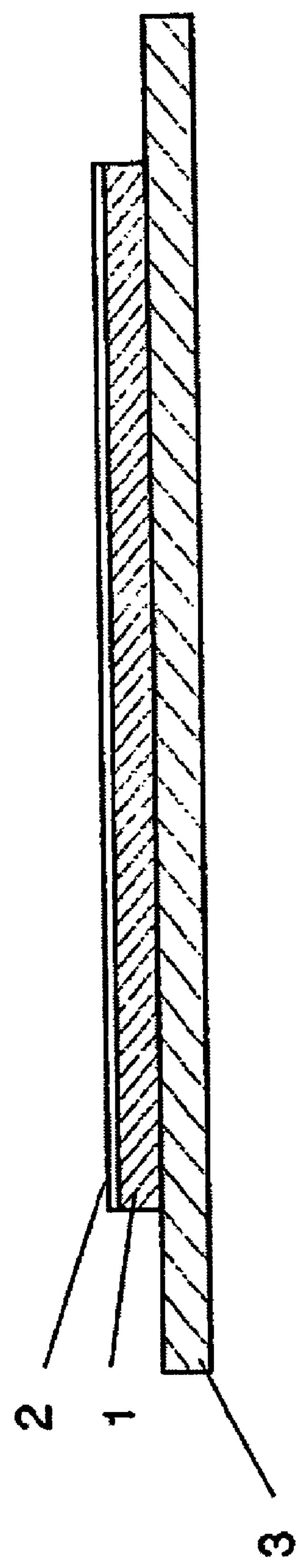
Figure 10: Schematic example of a TTS configuration

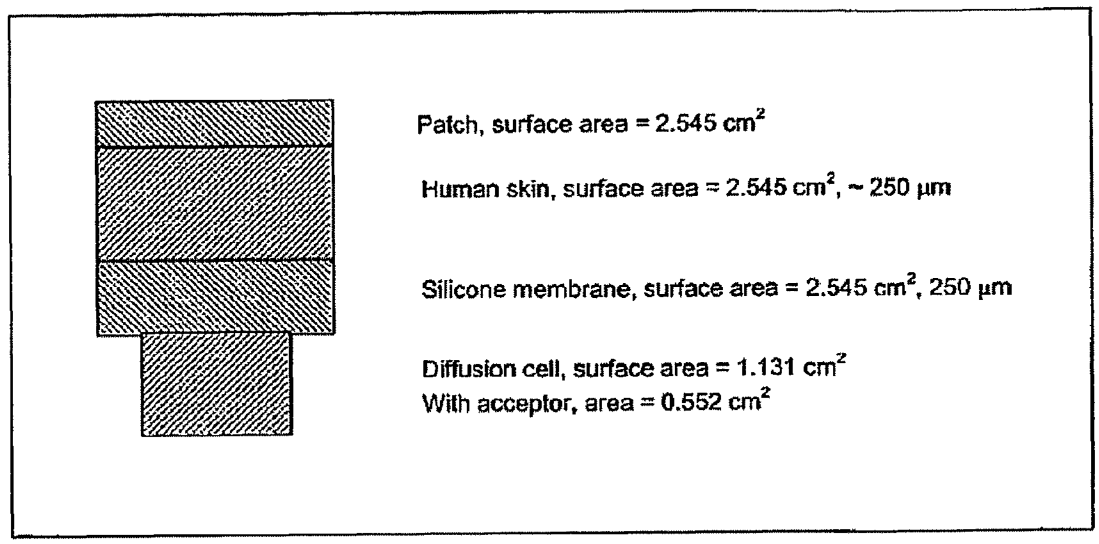
Figure 11: Diagram of a human-skin model used to determine rotigotine flux

HOT-MELT TTS FOR ADMINISTERING ROTIGOTINE

CROSS-REFERENCE TO RELATED APPLICATIONS

This application claims the benefit of U.S. provisional application Ser. No. 60/453,498 filed on Mar. 11, 2003, and of German application No. DE 102 34 673 filed on Jul. 30, 2002, both of which are incorporated herein be reference in their entirety. This application is related to U.S. Ser. No. 10/523,908 filed on Jul. 29, 2003.

FIELD OF THE INVENTION

This invention relates to a transdermal therapeutic system (TTS) encompassing a rotigotine-containing cement matrix, characterized in that the cement matrix contains a hot-meltable adhesive in which the active substance rotigotine ((−)5,6,7,8-tetrahydro-6-[propyl[2-(2-thienyl)ethyl-)amino]-1-naphthol) is dispersed and partly or completely dissolved.

The invention further relates to a method for producing a TTS that encompasses a cement matrix containing rotigotine as the active substance, characterized in that, prior to the coating and laminating, the components of the cement matrix are melted and homogenized, without any solvent, at temperatures between 70 and 200° C. and preferably between 120 and 160° C.

Finally, this patent application relates to the use of rotigotine for producing the cement matrix of a TTS by the hot-melting process.

BACKGROUND

Prior art has described various TTSs for the administration of rotigotine.

WO 94/07468 discloses a system that contains as the active substance a salt in a diphasic matrix.

That diphasic matrix consists of a hydrophobic polymer in which a silicate is dispersed to accept the hydrophilic medicinal salt, assisted by the additional use of organic solvents. The matrix is produced by drying the dispersion at 70° C. The rotigotine content in the matrix is 2-5% by weight.

That system, however, has a number of drawbacks:

(1) Its production is a multi-stage, complex process. The active substance must be dissolved in water or in an aqueous solvent mixture, then mixed with the silicate, then mixed with an emulsifier so as to finally emulsify the aqueous solution with the polymer such as a silicone cement dissolved in an organic solvent, typically heptane, ethyl acetate or toluene. The resulting emulsion is difficult to manipulate.

(2) Organic solvents are used which, during the TTS production, have to be completely removed again so as to ensure an adequate shelf life as well as reproducible release characteristics of the TTS while preventing skin irritations. That increases the production cost. Up to the point where the cement contains the active substance, it is a discontinuous process.

(3) Handling organic solvents requires stepped-up safety precautions to prevent any environmental impact or exposure of the personnel involved in the TTS production. Solvent recovery/separation equipment, measures for personnel protection and the disposal of solvents are all costly.

(4) On the one hand, the admixture of the active substance is limited by the degree of solubility of the rotigotine in the solvent concerned. On the other hand, as the solvent is removed during the production process, the relative concentration of the active substance increases, which can lead to an oversaturation of the matrix and to an undesirable formation of crystals. This again places a limit on the maximum amount of the active substance that can be worked into the matrix. Yet a low-level infusion of the active substance limits the release capacity of the matrix per unit of time and/or its functional lifespan due to a premature depletion of the active substance.

(5) The thickness of the matrix that can be obtained in one production step is limited to about 100 μm (equaling about 100 g/m$^2$) if it is to ensure the complete removal, in the drying process, of the solvent needed for its production. If cement matrices with a thickness greater than about 100 μm are required, they must be built up layer by layer, which is a complex and cost-increasing operation.

(6) The silicate or silicon oxide remaining in the adhesive patch constitutes a diffusion barrier for the active substance and may negatively affect the release of the latter. It also affects the water absorption of the adhesive patch. The formation of pores by the removal of water-soluble matrix components at the interface with the skin can lead to an insufficiently controllable release of the active substance.

WO 99/49852 describes a TTS with rotigotine in its free-base form containing an acrylate- or silicone-based adhesive system. For producing either system, solvents are again used that will later have to be removed again, involving the same drawbacks and limitations described under (2) to (5) above.

In terms of the infusion and release of rotigotine, the two matrices described in WO 99/49852 have these additional shortcomings:

Silicone matrices: Assuming an emulsion or solution containing an active substance, the matrix can accept rotigotine at about 15% by weight. In other words, there are limits to the admixability of active substances in silicone matrices. Increasing the rotigotine admixture for instance in the production of multi-day patches is possible only by adding more matrix layers, which, however, requires several procedural steps that make the production more complex and expensive.

Acrylate matrices: By means of solvent coating, acrylate matrices can accept rotigotine at up to about 40% by weight. However, the higher absorption capacity of these matrices for rotigotine is offset by a reduced capacity to release it onto the skin due to an agent-distribution coefficient that is inferior to that of silicone systems. Obtaining adequate rotigotine plasma levels from these systems requires very high charge rates. Yet relatively large amounts of the active substance remain in the patch after its use, increasing the effective cost of these systems while being undesirable from the perspective of drug safety.

It is therefore the objective of this invention to provide a TTS that avoids the drawbacks and limitations associated with the use of solvents. In particular, the rotigotine TTS should offer the highest possible degree of flexibility in admixing rotigotine even in larger amounts while releasing the rotigotine in therapeutically effective quantities.

The problems described above have been solved by providing, as the first of its kind, a TTS with a rotigotine-containing cement matrix, characterized in that the cement matrix is produced in a hot-melting process, whereby the cement matrix contains a hot-meltable adhesive in which rotigotine as the active substance ((−)-5,6,7,8-tetrahydro-6-

[propyl[2-(2-thienyl)ethyl-)amino]-1-naphthol) is dispersed and partly or completely dissolved.

BRIEF DESCRIPTION OF THE DRAWINGS

FIGS. 1*a* and *b* show comparisons of rotigotine permeation through murine skin (HMS), between a hot-melt silicone TTS and a solvent-based silicone TTS. FIG. 1*a* illustrates the release from either TTS each with a rotigotine content of 9% by weight. FIG. 1*b* shows the effect of a higher rotigotine charge on the rotigotine permeation from the hot-melt TTS through the murine skin.

FIG. 2 shows the effect of the wax content on the permeation through murine skin of rotigotine from the hot-melt silicone TTS with a constant 9 weight % charge of the active substance.

FIGS. 3*a* and *b* show the effect of the rotigotine charge on the rotigotine permeation through murine skin from the silicone-based hot-melt TTS in the presence of 15% wax (3*a*) and, respectively, 5% wax (3*b*).

FIG. 4 illustrates the effect of the matrix weight on the rotigotine permeation through murine skin from a silicone-based hot-melt TTS.

FIGS. 5*a* and *b* show the effect of the content of the internal-phase component on the cumulative (5*a*) and linear (5*b*) permeation of rotigotine from the hot-melt TTS through murine skin.

FIG. 6*a* shows the cumulative 72-hour permeation of rotigotine from a hot-melt silicone TTS through human skin in comparison with that from a solvent-based silicone TTS. FIG. 6*b* shows the cumulative 7-day permeation of rotigotine from a hot-melt silicone TTS through human skin.

FIG. 7 shows the cumulative rotigotine permeation, from hot-melt TTS with different hot-meltable cements, through murine skin.

FIG. 8 shows the cumulative permeation, through murine skin, of rotigotine from silicone-based hot-melt TTS produced in an extruder with different internal-phase components and a rotigotine content of 9%.

FIG. 9 shows the cumulative permeation, through murine skin, of rotigotine from EVA-based hot-melt TTS produced in the extruder with different rotigotine concentrations.

FIG. 10 illustrates an example of a TTS structure with an active substance-containing cement matrix (1), a backing (2) that is inert to the constituent components of the cement matrix, and a protective film (3) that must be removed before use.

FIG. 11 is a diagram of a human-skin model used to determine rotigotine flux as described in Example 9.

DESCRIPTION OF THE INVENTION

It was surprising to find that rotigotine lends itself superbly to processing by the hot-melt method, that it remains stable under short-term heating to temperatures up to at least 160° C., that it can be homogeneously worked into matrices produced by the hot-melt process, and that it is released from the hot-melt matrices in continuous fashion and at a therapeutically desirable rate.

In particular, the inventors were surprised to find that the rotigotine, being susceptible to oxidation, remains stable in the hot-melt process even when heated to temperatures around 160° C. While at higher temperatures in an oxygen-containing atmosphere, rotigotine tends to decompose in oxidative fashion, it is amazingly stable in the hot adhesive melt and is present in the matrix at a purity level that is routinely better than 98% and generally over 99% (measured at 220 nm and 272 nm per HPLC; see tables 2, 3 and 4).

The preferred method is to introduce the rotigotine in its solid form into the homogenized matrix melt, i.e. the rotigotine is not melted until it is in the hot matrix. Following brief homogenization the rotigotine-containing cement matrix is cooled again so that, in general, the rotigotine is exposed to thermal stress for less than 5 minutes and preferably less than 4, 3 or even 1 minute(s). The rotigotine will then be present in the solidified melt. During that process the rotigotine is largely protected from critical environmental factors (light, oxygen).

The TTSs thus produced by the hot-melt method accept a high rotigotine charge of up to 40% by weight relative to the weight of the matrix.

Overall, the TTSs produced according to this invention by the hot-melt method offer a number of advantages over prior-art solvent-based TTSs:

- Since the rotigotine can be directly inserted in the adhesive melt, it eliminates the solvent-related problems when higher active-substance concentrations are used. Consequently, substantially higher rotigotine concentrations (up to over 40 weight %) can be introduced in the TTS, in simple fashion, than would be possible in a solvent- and silicone-based process where rotigotine concentrations of more than about 15 weight % can no longer be worked in as a solution. It is thus possible to introduce surprisingly large rotigotine amounts even in relatively thin matrices, and in only one procedural step.
- The thickness of the layer can be varied over a wide range. For example, matrices having a weight of more than 100 $g/m^2$ and even more than 200 $g/m^2$ can be produced in a single step without difficulty. It follows that, in combination with the higher rotigotine concentration, a rotigotine content in the TTS matrix of up to 8 $mg/cm^2$ or even more is attainable. In contrast to that, it is not possible in a single-step operation to introduce a rotigotine charge of more than about 1.5 $mg/cm^2$ in a silicone TTS produced by the solvent-based process.
- The use, removal, recovery or disposal by incineration of organic solvents and the associated need for safety precautions in TTS production are eliminated.
- Hot-melt technology permits the continuous production of the TTS matrix from the weighing of its individual components all the way to lamination. That type of production cycle essentially offers the following advantages:
  - Processing times are substantially reduced.
  - The charge volume is determined via the operating time of the production facility. This avoids having to switch over to larger facilities with the associated scale-up problems and/or additional validation requirements.
- GMP-compliant production is possible using compact equipment with a small footprint.
- Using a suitable softener such as wax or the optional incorporation of an internal phase permits delayed release of the rotigotine from the cement matrix. An appropriate TTS configuration makes it possible to produce TTSs that release rotigotine over a span of several days, for instance 5, 6 or 7 days, in continuous fashion and therapeutically effective quantities.

Therefore, one object of this invention is a transdermal therapeutic system (TTS) that encompasses a rotigotine-containing cement matrix, characterized in that the cement matrix contains a hot-meltable adhesive in which the active substance, rotigotine ((−)-5,6,7,8-tetrahydro-6-[propyl[2-(2-thienyl)ethyl-)amino]-1-naphthol), is dispersed and partly or completely dissolved.

Another object of this invention is a TTS with a rotigotine-containing cement matrix produced by the hot-melt method employing a process in which the rotigotine is introduced, in molten or preferably in its solid form, into the 70-200° C. melt of the solvent-free cement matrix. The rotigotine is introduced in a solvent-free melt that is preferably heated to 100-170° C., desirably to 120-160° C. and ideally to 130-150° C., and then processed and cooled within 5 minutes, preferably within 3 minutes and ideally within a maximum of 1 minute after the admixture of the rotigotine.

The term "transdermal therapeutic system" refers to a pharmaceutical formulation or device that lends itself to the transdermal administration of an active substance through the skin of a mammal, especially through the human skin, in therapeutically effective quantities.

The term "hot-melt process" refers to a method that employs thermal energy for melting the hot-meltable adhesive and the optionally provided internal phase, thus obviating the need for solvents in the production of the cement matrix. By "hot-melt process" this patent application also subsumes a procedural variation involving work at temperatures below the melting point of rotigotine, whereby the adhesive melt contains the rotigotine in its solid form.

The term "solvent-free" as used in this patent application indicates that in producing the cement matrix no solvents are used that would have to be removed again in the course of the production process.

The term "hot-meltable adhesive" refers to an adhesive which, when applied to the skin, is pressure-sensitive and which can be processed by the hot-melt method at process temperatures of 70° C. to 200° C., preferably 100° C. to 170° C., desirably 120° C. to 160° C. and ideally at temperatures between 130° C. and 150° C. The "hot-meltable adhesive" may consist of an adhesive or a mixture of different adhesives that are individually hot-meltable. Alternatively, the "hot-meltable adhesive" may be a mixture composed of an adhesive and a suitable softener.

These hot-meltable adhesives preferably have a dynamic viscosity which at 160° C. and especially at temperatures between 130° C. and 150° C. is at the most 150 Pa, preferably not more than 120 Pa, desirably less than 100 Pa and ideally less than 80 or even 60 Pa.

Examples of adhesives that are not hot-meltable per se include the commercially available silicone adhesives. At the aforementioned processing temperatures, silicone adhesives would be too viscous, having a dynamic viscosity of more than 150 Pa.

Existing patent literature discusses a variety of methods for making highly viscous silicone adhesives hot-meltable by admixing suitable additives (softeners). Examples of such softeners for silicones include glycerol monolaurate or lauryl acetate as described in EP 835 136, waxes along the formula R—C(O)—OR' as described in EP 360 467, alkylmethyl siloxane waxes as described in EP 524 775, siloxated polyether waxes as described in EP 663 431, or organic waxes as described in U.S. Pat. No. RE 36,754.

The softeners are usually added to the silicone adhesive in quantities from 1-30 weight % relative to the overall hot-meltable cement mixture. The preferred softeners are organic waxes as described in U.S. Pat. No. RE 36,754, such as ozokerite, ceresine, paraffin, candelilla, carnauba, bee's wax or mixtures of these waxes, with ozokerite and ceresine being particularly preferred.

Ready-mixed hot-meltable silicone adhesives, especially mixtures of silicone adhesives and ceresine or ozokerite, are available from Dow Corning in Michigan. Adding for instance 10 weight % of ceresine to a silicone adhesive succeeded in reducing the dynamic viscosity of the resulting adhesive mixture, at a processing temperature of 160° C., from over 150 Pa to below 50 Pa. That type of silicone-based adhesive mixture lends itself well to being processed by the hot-melt method within a temperature range from 100° C. to 200° C. and especially in the range between 120° C. and 160° C.

A surprising discovery showed that hot-meltable silicone adhesives are superbly suitable for the transdermal administration of rotigotine.

Therefore, one object of this invention is a transdermal therapeutic system (TTS) that encompasses a rotigotine-containing cement matrix, characterized in that the cement matrix contains a hot-meltable adhesive in which the active substance, rotigotine ((−)-5,6,7,8-tetrahydro-6-[propyl[2-(2-thienyl)ethyl-)amino]-1-naphthol), is dispersed and partly or completely dissolved, said hot-meltable adhesive containing a suitable mixture of a silicone-based adhesive and at least one softener.

Another aspect of this invention consists of a TTS that encompasses a cement matrix containing:

(a) 50-99 weight % of an adhesive mixture composed of (i) 70-99 weight % of an amine-resistant silicone adhesive and (ii) 1-30 weight % of a suitable softener, and (b) 1-40 weight % rotigotine.

In a preferred implementation of the invention, the said silicone-based hot-meltable adhesive consists of (a) 70-99 weight % of an amine-resistant silicone adhesive and (b) 1-30 weight %, preferably 3-15 weight % and most desirably 4-10 weight % of an organic wax ideally selected from the group encompassing ozokerite, ceresine, paraffin, candelilla, carnauba, bee's wax or mixtures of these waxes, with particular preference given to ozokerite and especially ceresine.

As shown in FIG. 1*a*, a silicone-based hot-melt TTS of this simple composition produces in-vitro rotigotine permeation rates comparable to those of prior-art, therapeutically effective, solvent-based silicone TTSs.

FIG. 1*b* shows that, with an appropriately high infusion of the hot-melt silicone TTS per this invention, in-vitro flux rates can be achieved that are clearly above the rates attainable with prior-art, clinically effective, solvent-based silicone patches.

For the purpose of this patent application the term "hot-melt TTS" refers to a TTS whose cement matrix was produced by the hot-melt method, meaning by the solvent-free melting of the hot-meltable adhesive and, where applicable, additional components.

A surprising discovery showed that adding wax, especially organic wax such as ceresine or ozokerite, also has an effect on the in-vitro murine-skin permeation of rotigotine from the hot-melt silicone TTS. As is evident from FIG. 2, rotigotine's permeation rate decreases as the wax concentration increases. This can be explained by a partial rotigotine distribution in the wax and a concomitant retardation effect.

This property of the wax is significant especially for developing a TTS designed for application over several days, for instance 7 days. That type of multi-day patch requires a high infusion of rotigotine, which poses the risk of an excessive release of rotigotine at the beginning of the application phase ("dose dumping"). It is therefore desirable to work into the TTS a component that controls the release of the active substance. This could be in the form of a membrane attached to the bottom of the matrix for controlling the release of the active substance. However, such a membrane increases material cost and makes the TTS structure more complex. It would therefore be desirable, instead of adding such a membrane, to include suitable retardant components in the matrix.

Apart from the surprising discovery that the wax content in the matrix serves to retard the release of the active substance, varying the wax content will not only modify the dynamic viscosity of the adhesive but additionally offers the equally surprising option of regulating the active-substance release.

As the wax content increases, the dynamic viscosity of the silicone adhesive initially drops off sharply to where the wax content is about 5 weight %, after which it decreases only slightly. Thus, when the wax content is 4-10 weight %, the dynamic viscosity of the silicone adhesive is at a level that suitably permits hot-melt processing while at the same time its effect on the rotigotine release is minor. Higher wax concentrations will additionally produce a retardation effect.

Similarly, the effect of the wax on the rheological properties of the TTS is surprising. If an organic wax is used as the softener for a silicone adhesive, the dynamic viscosity of the adhesive mixture decreases at elevated temperatures, which in excellent fashion permits the processing of the silicone-based cement mixture by the hot-melt method. At the same time, the rheological properties of the silicone, such as its cohesivity, unexpectedly remain fairly unaffected at room temperature, so that the typical problems with hot-meltable adhesives such as cold flux on the patient's skin are not encountered.

Suitable silicones include all of the silicone adhesives employed in adhesive-patch technology. The preferred silicone adhesives are amine-resistant, pressure-sensitive polyorganosiloxane adhesives.

In most cases, the silicone adhesives are polydimethyl siloxanes, but in principle it is just as possible to use in place of the methyl groups other organic radicals such as ethyl or phenyl groups.

Amine-resistant silicone adhesives generally offer the advantage that they contain no or only few free silanol functions since their Si—OH groups were alkylated. That type of adhesives has been described in EP 180 377. The particularly preferred adhesive cements include condensates or mixtures of silicone resins and polyorganosiloxanes as described for instance in U.S. Pat. No. RE 35,474.

These silicone adhesives are commercially available and are marketed for instance by Dow Corning as Bio-PSA Q7-4300 or Bio-PSA Q7-4200. Also available from Dow Corning are hot-meltable silicone adhesives that are mixtures of PSA 7-4300 with organic waxes such as ozokerite or ceresin.

The active substance, rotigotine, may be present at concentrations of 1 to more than 40 weight % relative to the weight of the total cement layer, either as a salt or in free-base form. Preferably, the cement matrix contains the rotigotine in free-base form.

Unlike the solvent-based silicone adhesives whose active-substance content is 15 weight % at the most, the adhesive matrices of hot-melt TTSs can accept significantly greater amounts of rotigotine without requiring any additional technical measures. That again provides greater flexibility in selecting the permeation rate and the release period of the hot-melt TTS.

As is evident from the example of a silicone-based hot-melt TTS in FIGS. 3*a* and 3*b*, a higher rotigotine charge allows for a higher flux rate through mammalian skin as well as a longer rotigotine release time. In applying a TTS on human skin, the particular effect of a higher rotigotine concentration is an extended rotigotine release while from an 8-9% rotigotine concentration on up the permeation rate through human skin increases only marginally.

The preferred rotigotine concentrations in the adhesive layer are 4-40 weight %, especially 9-30 weight % and more specifically 9-25 weight % or 15-25 weight %, for 7-day patches they are 20-40 weight % and especially 25-35 weight %, relative to the total weight of the adhesive layer.

Varying the layer thickness of the cement matrix serves as an additional element in controlling the rotigotine release rate and duration. The example of a hot-melt silicone TTS in FIG. 4 shows the effect of the weight of the matrix on the in-vitro permeation of rotigotine through murine skin.

The thickness of the cement matrix can be flexibly selected over a wide range and in one singlμμe procedural step, since the layer thickness is not subject to the limitations associated with the solvent-based method. The layer thickness may be between 30 and 300 μM, preferably between 50 and 150 μm and most desirably between 50 and 120 μM.

The weight of the cement matrix of the TTS according to this invention is preferably between 30 and 300 g/m$^2$, desirably between 50 and 150 g/m$^2$ and ideally between 50 and 120 g/m$^2$; for 7-day patches it is preferably 70-200 g/m$^2$, desirably 80-180 g/m$^2$ and ideally 100-160 g/m$^2$.

The preferred rotigotine content in the matrix is between 0.4 mg/cm$^2$ and 8 mg/cm$^2$, depending on for how long the TTS is to be applied.

For a 1-day TTS the preferred concentration is between 0.4 and 1.5 mg/cm$^2$ and most desirably between 0.4 and 0.8 mg/cm$^2$.

The average therapeutically required dose is about 6 mg of rotigotine per day. Hence, a 7-day patch requires about 42 mg of the active substance per TTS. For safety considerations, clinically employed transdermal systems are assumed to draw only about 50-60% of the TTS supply, which is why a 7-day TTS should contain at least 70 to 80 mg of the active substance.

Consequently, given a 7-day-patch TTS size of preferably 10-30 cm$^2$ and most desirably 15-25 cm$^2$, the preferred rotigotine charge will be as follows:

| Patch Size in cm$^2$ | Minimum Rotigotine Content in mg/cm$^2$ |
|---|---|
| 10 | 7.0-8.4 |
| 15 | 4.7-5.6 |
| 20 | 3.5-4.2 |
| 25 | 2.8-3.4 |
| 30 | 2.3-2.8 |

Accordingly, the preferred rotigotine content in 7-day patches is between about 2 mg/cm$^2$ and 8 mg/cm$^2$, desirably between about 2.8 mg/cm$^2$ and 5.6 mg/cm$^2$ and ideally between 3.1 and 5.6 mg/cm$^2$.

So far, prior art has not disclosed any TTS for the administration of rotigotine in therapeutically significant quantities at this high level, which at this point is possible only by the variable charging and layer thickness of the hot-melt TTS. The high rotigotine concentration of up to over 40 weight % makes it possible even for a 7-day TTS containing an appropriately large amount of rotigotine to produce relatively thin matrices with a layer thickness of 80-200 μm, preferably 80-180 μm and ideally 80-160 μm.

Another object of this invention therefore includes TTSs for the administration of rotigotine in therapeutically effective quantities, characterized in that they feature a rotigotine concentration in the cement matrix of at least 2.0 mg/cm$^2$, preferably at least 2.8 mg/cm$^2$ and most desirably at least 3.1 mg/cm$^2$ or at least 3.4 mg/cm$^2$. Preferred are TTSs containing matrices with a rotigotine change rate of over 20 weight % and a matrix weight of under 200 g/m$^2$, for instance a weight of between 80 and 180 g/m$^2$ and most desirably between 80 and 160 g/m$^2$.

As an option, the cement layer (also referred to as the cement matrix) may contain, in addition to the rotigotine and the adhesive mixture, a component that serves as the internal phase.

In particular, the internal-phase component serves as a solubilizer and crystallization inhibitor while contributing to a uniform distribution of the active substance in the cement matrix. The internal-phase component also helps augment moisture absorption of the patch on the skin.

For use in the hot-melt process, the most suitable internal-phase components are those exhibiting at temperatures below 170° C. a dynamic melting viscosity of not more than 150 Pa, preferably less than 120 Pa and most desirably less than 80 Pa.

If at the desired processing temperature the dynamic viscosity of the internal-phase component is too low, a suitable softener such as glycerin may first have to be added. In some cases the active substance, rotigotine, may itself have softening properties. This is the case for instance with polyvinyl pyrrolidone so that, when PVP is to be metered into an extruder, a PVP/rotigotine premelt can be produced.

The internal-phase components are preferably selected out of the group of (a) hydrophilic or amphiphilic polymers, (b) hydrophilic or amphiphilic copolymers, (c) mixtures of (a) and/or (b) with pharmaceutically acceptable softeners, (d) condensates from glycerin with fatty acids or polyols, and (e) suitable mixtures of the substances (a)-(d).

Internal-phase components suitable for use in the TTS per this invention may be selected, for instance, from the group of polysaccharides, substituted polysaccharides, polyethylene oxides, polyvinyl acetates, polyvinyl pyrrolidones (PVP), PVPs with suitable softeners, polyethylene glycols, polypropylene glycols, acrylates, copolymers from polyvinyl pyrrolidone and (poly)vinyl acetate, copolymers from ethylene and vinyl acetate, as well as polyvinyl alcohols with a suitable softener such as glycerin.

The preferred internal-phase components are PVP, PVP with softener, polyethylene oxides (PEO), polyvinyl acetates (PVA), and copolymers from PVP and vinyl acetate.

The internal-phase component is added to the cement layer at a concentration of 0-40 weight % as related to the overall weight of the cement layer, with the preferred amount of the added internal-phase component being 2-25 weight %.

A surprising discovery was made whereby, given a constant amount of the active substance and perhaps a softener, the internal-phase component not only promotes the solubility of the rotigotine and thus its uniform distribution in the matrix but, as the quantity is increased, it also leads to a retardation, i.e. linearization, of the rotigotine release.

Using the example of a silicone-based hot-melt TTS, FIGS. 5*a* and 5*b* show the effect of the PVP content on the in-vitro rotigotine permeation through murine skin. As the PVP content is increased, it leads to a linearization of the rotigotine permeation rate (FIG. 5*a*) that is attributable to a significant reduction of the initial release of the active substance (FIG. 5*b*).

This retardation effect of the internal-phase component can be utilized for instance in the case of hot-melt TTSs with a high active-substance charge for producing a patch that releases the active substance, rotigotine, in uniform, therapeutically effective quantities over an extended period such as at least 3 days, or at least 4, 5, 6 or 7 days.

Assuming an average daily dose of 6 mg rotigotine, the necessary hourly steady-state rotigotine flux rate will be 250 μg. For a TTS with a surface area of between 10 and 30 cm$^2$ that means a necessary flux rate of 8.3-25 μg/cm$^2$/h.

In in-vitro permeation experiments on human skin with the disclosed silicone-based hot-melt TTS having a rotigotine charge of about 23-25 weight % and a patch weight of 54-84 g/m$^2$, i.e. a rotigotine content of 1.2-2.1 mg/cm$^2$ of matrix, it was possible to achieve continuous flux rates of 12-16 μg/cm$^2$/h over a period of at least 3 days (see FIG. 6*a*).

That flux rate was on the order of magnitude of the clinically relevant flux rate obtained with the comparative silicone-based TTS produced by the solvent method. After about 48 hours, with the active-substance supply exhausted, the permeation curve of the comparative TTS broke off while the supply of the more highly charged hot-melt TTS was not exhausted even after 72 hours.

Applying the hot-melt TTS according to this invention on a human skin model as described in Implementation Example 9, a rotigotine concentration of 25 weight % and a matrix weight of 85 μm$^2$ made it possible, after an initial lag phase, to maintain a 7-day steady-state flux rate through the human skin of about 15 μg/cm$^2$/h (FIG. 6*b*).

Therefore, one object of this invention is a TTS whose cement matrix contains rotigotine as the active substance in an amount of at least 20 weight %, and preferably over 25 weight %, and which, in an in-vitro permeation test on human skin as described in Implementation Example 9, leads to a continuous flux rate of at least 8 μg/cm$^2$/h, or preferably 10 μg/cm$^2$/h, lasting over a period of at least 5, 6 or 7 days.

Another object of this invention is a hot-melt TTS that contains rotigotine as the active substance in its adhesive layer in an amount of at least 20 weight % and preferably at least 25 weight % and which, in an in-vitro permeation test on human skin as described in Implementation Example 9, attains a continuous flux rate of at least 8 μg/cm$^2$/h for a period of at least 7 days.

For standardizing the solvent-based, rotigotine-containing silicone TTS, the in-vitro model per Tanojo (*J Contr. Release* 45 (1997) 41-47), used for measuring the flux rate through the human skin, has proved to be a good model for predicting the in-vivo flux rate determined in clinical studies. In contrast to a few other in-vitro human-skin models employed for comparison purposes, the flux rates through the human skin as determined by the Tanojo model correlated excellently with the results obtained in clinical studies (Phase III) in terms of flux rates, plasma levels and clinical parameters such as the UPDRS score.

The results obtained with the model described in Implementation Example 9 therefore suggest that the hot-melt TTS is equally suitable for the in-vivo administration of rotigotine in therapeutically effective amounts over a period of several days.

In clinical practice, the flux is preferably set at a rate where the patient maintains a continuous therapeutic plasma level of between 0.4 and 2 ng/mL of blood. This requires an hourly rotigotine flux through the patient's skin of 100-400 μg, preferably about 200-300 μg (corresponding to 10-15 μg/cm$^2$/h for a 20 cm$^2$ TTS), desirably 230-270 μg and ideally about 250 μg. The standard dosage may be varied especially in adaptation to the patient's physical constitution. As shown in FIG. 6*b*, this flux rate is achievable over a 7-day period employing the TTS according to the invention.

Thus, for the first time, a TTS for the continuous transdermal administration of rotigotine is provided which, when applied on human skin, induces an average plasma concentration of 0.4-2 ng/ml rotigotine over a period of at least 5, 6 or 7 days.

Also for the first time, a TTS is provided that is capable of administering rotigotine through mammalian and especially human skin at an hourly flux rate of 200-300 μg over a period of 5, 6 or 7 days.

Therefore, one aspect of this invention is a TTS, preferably a hot-melt TTS and especially a silicone-based hot-melt TTS, that lends itself to the continuous administration of rotigotine over a period of at least 5, 6 or 7 days at a steady-state flux rate of 200-300 μg/day.

Another aspect of this invention is a TTS, preferably a hot-melt TTS and especially a silicone-based hot-melt TTS, that lends itself to the continuous administration of rotigotine to humans over a period of at least 5, 6 or 7 days, where over at least 80%, preferably at least 90% and most desirably at least 95% of the time selected the plasma level in the patient's circulatory system is set at between 0.4 and 2 ng rotigotine per mL of blood.

Another object of this patent application is a TTS for the transdermal administration of rotigotine, encompassing an active-substance-containing layer, characterized in that:

(a) the active-substance-containing layer
   (a1) incorporates a rotigotine component of at least 20 weight % and preferably at least 25 weight %,
   (a2) has a rotigotine concentration of at least 2.0 mg/cm$^2$, preferably 2.8 mg/cm$^2$ and most desirably at least 3.1 mg/cm$^2$ or at least 3.4 mg/cm$^2$, and
   (a3) optionally contains an amount of an active-substance-retardant organic wax and/or an internal-phase component, and
(b) upon application of the TTS on the patient's skin, will transcutaneously dispense rotigotine over a period of at least 5 days and preferably at least 7 days at a steady-state flux rate of 100-500 μg/hour and preferably 200-300 μg/hour.

Another object of the invention is a rotigotine-containing TTS, preferably a rotigotine-containing hot-melt TTS and, most desirably, a rotigotine-containing silicone-based hot-melt TTS, characterized in that:

(a) the rotigotine is contained in the cement matrix in an amount of at least 20 weight % and preferably at least 25 weight %,
(b) the cement matrix has a rotigotine content of at least 2.0 mg/cm$^2$, preferably 2.8 mg/cm$^2$ and most desirably at least 3.1 mg/cm$^2$ or at least 3.4 mg/cm$^2$, and
(c) rotigotine is released to the patient over a period of at least 5, 6 or 7 days at a steady-state rate of at least 100-500 μg/hour, preferably 200-300 μg/hour and most desirably 230-270 μg/hour.

Those skilled in the art are familiar with other additives that may in principle be contained in the cement layer, such as antioxidants, stabilizers, tackifiers, preservatives or permeation boosters.

Whether the addition of such substances to the essential components per this invention, as defined in the claims, is useful in any given case can be determined by routine tests and such implementations are therefore specifically made a part of this invention.

In one preferred form of implementation of the invention the disclosed hot-melt TTSs do not contain any permeation boosters.

One form of implementation of the invention is therefore a hot-melt TTS encompassing a cement matrix that contains:

(a) 50-99 weight % of a hot-meltable adhesive,
(b) 1-40 weight %, preferably 5-30 weight %, desirably 9-30 weight % and ideally 15-25 weight % of rotigotine,
(c) 0-40 weight %, preferably 2-25 weight % and most desirably 5-25 weight % of an internal-phase component preferably selected from among the group of polysaccharides, substituted polysaccharides, polyethylene oxides, polyvinyl acetates, polyvinyl pyrrolidones with or without softeners, polyethylene glycols, polypropylene glycols, acrylates, copolymers from polyvinyl pyrrolidone and polyvinyl acetate, copolymers from ethylene and vinyl acetate, as well as polyvinyl alcohols with a softener such as glycerin; and
(d) 0-10 weight %, preferably 0-5 weight % and most desirably 0-3% of other additives such as tackifiers, antioxidants, stabilizers, and permeation boosters, where the hot-meltable adhesive (a) is preferably a mixture of (i) 70-99 weight % of an amine-resistant silicone adhesive and (ii) 1-30 weight % of a suitable softener, especially a wax, preferably an organic wax and most desirably ozokerite or ceresin.

Referring to FIG. 10, the hot-melt TTS may consist exclusively of the cement matrix, but in addition to the rotigotine-containing cement matrix it preferably includes such components as a backing (2) that is impermeable to the active substance and inert to the components of the cement matrix, and a protective foil (3) that covers the cement matrix (1) and must be removed before use. Those skilled in the art are familiar with other possible variations of the TTS configuration, including for instance an added membrane that controls the flux of the active substance, and/or an added adhesive foil ("overtape"). Particular preference is given to the "monolithic" TTS configuration depicted in FIG. 10.

Rotigotine is a dopamine agonist. Therefore, the TTS according to the invention is especially suitable for the treatment of diseases associated with dopamine-metabolic disorders, most particularly Parkinson's disease or Restless Leg.

One object of the invention, therefore, is a method for treating dopamine-metabolic diseases, especially Parkinson's disease or Restless Leg syndrome, characterized in that a rotigotine-containing hot-melt TTS according to this invention is applied on the skin of a patient.

Another object of the invention is a product package holding one or several rotigotine-containing hot-melt TTSs per this invention as well as instructions for their use.

So far, the only methods known from prior art for the production of rotigotine-containing TTSs have employed a solvent-based rotigotine-containing cement matrix, requiring the removal of the solvent from a solvent-containing silicone- or acrylate-based dispersion. This present invention is the first to introduce a solvent-free hot-melt method for producing a rotigotine-containing TTS.

Therefore, one aspect of this invention is a method for producing a TTS encompassing a cement matrix that contains rotigotine as the active substance, characterized in that, prior to being laminated onto a foil, the components of the cement matrix are melted and homogenized, solvent-free, at temperatures of between 70 and 200° C., preferably between 100 and 200° C. and most desirably between 120 and 160° C. The ideal operating temperature in the extruder is between 130 and 150° C.

Surprisingly, it was found that, after the melting, the rotigotine remains stable in a variety of matrices even without the addition of stabilizers or antioxidants. HPLC measurements with UV analyses at 220 nm and 272 nm have shown that even without the admixture of antioxidants the purity level of the active substance routinely remained above 98% and generally better than 99% (Tables 2-4; Implementation Examples 4, 6 and 7).

Therefore, one aspect of the invention is the use of rotigotine in the production of a TTS, characterized in that the rotigotine is infused in the cement layer of the TTS by the hot-melt method.

It is entirely possible to introduce the rotigotine in the matrix either premelted or by metering it in solid form into the hot matrix melt where it is melted.

In a preferred form of implementation the rotigotine is melted at temperatures between 100 and 200° C., preferably between 120 and 160° C. and desirably between 130° C. and 150° C., in that rotigotine in its solid state is metered into the molten matrix, optionally without the addition of stabilizers or antioxidants.

In a particularly preferred form of implementation the rotigotine is melted by metering it, in its solid state, into the hot molten matrix and by briefly homogenizing and then calendering the rotigotine-containing matrix melt onto a foil substrate where it is cooled. In that operation the rotigotine is exposed, preferably for a maximum of 5 minutes and most desirably for less than 4, 3, 2 or even 1 minute(s), to a temperature of 100° C. to 200° C., preferably 120-160° C. and ideally 130-150° C.

Another aspect of this invention is, therefore, the use of rotigotine for producing a TTS by the hot-melt method at temperatures of between 120 and 160° C. and most preferably at 130° C. to 150° C., whereby the hot-melt process produces a cement matrix containing rotigotine at a purity level of at least 98% and preferably 99% as measured at 220 and 272 nm.

In another form of implementation of the invention, the cement layer of the TTS is melted at very low temperatures of 70-75° C., which is just below the melting point of rotigotine. That leaves the rotigotine in the matrix in its solid state. This method requires the use of hot-meltable adhesives that permit processing at 70° C., while on the other hand the dynamic viscosity of the adhesive mixture must not be set too low to avoid cold flux of the adhesive layer on the skin. The process therefore requires the application of a fairly high shearing force.

Therefore, one aspect of this invention is the production of a TTS by the hot-melt method, whereby the cement layer is melted at temperatures below the melting point of rotigotine, meaning below about 75° C., and the rotigotine in its solid state is metered into the melt.

For the industrial production of the TTS the cement layer is preferably prepared in an extruder. In that process, the individual components of the cement layer can be introduced in the extruder, for instance a dual-screw extruding machine, via the respective feed channels either separately or in premixed form. The combined substance is mixed in the extruder under controlled heating conditions, whereupon it can be continually processed and ultimately laminated.

Since at room temperature the hot-meltable adhesive remains solid, premelting is necessary. That can be accomplished for instance by means of a melting/metering system consisting of a container with controlled heating, in which the hot-meltable adhesive such as the hot-meltable silicone adhesive is premelted at temperatures between 70° C. and 200° C., preferably between 100° C. and 170° C., desirably between 120° C. and 160° C. and ideally between 130 and 150° C. The melting/metering system permits continuous feeding, allowing it to be easily integrated into the continuous production system. The metering section may be of the volumetric or gravimetric type.

In hydrophobic adhesives such as silicones, rotigotine is soluble in trace amounts only, which is why it must be dispersed. The viscosity of the molten rotigotine is very low, as a result of which there may be considerable viscosity differences during the process between the adhesive and the active substance. For optimizing the distribution of the active substance in the cement matrix, one has the option of integrating static mixing agents in the extrusion process to ensure an even more homogeneous blending of the cement matrix. Suitable static mixing agents are available for instance from Sulzer Chemtech GmbH. It has thus been possible, as verified by microscope analyses of the cement matrix, to reduce the droplet size of the active-substance particles and of the internal-phase domains to an average of less than 20 μm.

There are several advantages to that:

For one, it prevents the formation of larger active-substance particles in the matrix that might lead to an uneven flux, to an adhesion/cohesion imbalance or to the recrystallization of the active substance.

For another, it prevents the accumulation of the active substance at the interface between the cement matrix and the skin that could cause skin irritation and/or protonation of the active substance with the consequent reduction of the flux rate through rediffusion of the protonized base.

Therefore, the size of the active microparticles should not exceed 80%, preferably 60% or ideally 50% of the thickness of the cement matrix. The average size of these microparticles is preferably in a range up to 40% and desirably up to 30% of the matrix thickness.

Assuming a matrix thickness for instance of 50 μm, the internal phase in the cement matrix would then preferably be in the form of droplets with an average size of up to 20 μm and preferably up to a maximum of 15 μm.

FIG. 8 shows the in-vitro permeation of rotigotine through murine skin from different silicone-based hot-melt TTSs produced by fused extrusion in an extruder under utilization of different internal-phase components.

Apart from the silicone-based adhesive systems, other hot-meltable adhesives are in principle equally suitable for use in the rotigotine-containing hot-melt TTSs according to this invention.

Hot-meltable adhesives have been described in prior art. Examples of usable types include hot-meltable adhesives based on styrene block copolymers ("SXS adhesives") derived from polymers with non-elastomeric styrene blocks at the ends and elastomer blocks in the middle. The elastomer blocks may consist for instance of polyethylene butyl, polyethylene propylene, polybutadiene or polyisopropene.

Adhesives of that type have been described for instance in U.S. Pat. No. 5,559,165 and U.S. Pat. No. 5,527,536. They offer good adhesive properties, are easy to produce and process and are well tolerated on the skin.

SXS adhesives can be procured commercially (e.g. as Duro Tak 378-3500 from National Starch & Chemical), or they can be produced using hot-melt extrusion equipment in the course of the production of the active-substance-containing patches. This involves the individual metering into and mixing and melting in the extruder of corresponding quantities (at least of the following components) of a styrene block copolymer (such as Shell Kraton GX1657 or Kraton D-1107CU) with a resin (such as Keyser-Mackay Regalite R1090 or Regalite R1010 or Regalite R1100) and an oil (such as Shell Ondina 933 or Ondina 941). As the last step, the active substance is metered into the adhesive thus produced in the extruder and the compound is then laminated onto a foil. Examples of typical polymer/resin/oil weight ratios are 100/120/20 or 100/200/50. By varying these ratios it is possible to adapt the properties of the SXS adhesive to the respectively desired properties of the TTS (adhesive strength, minimal cold flux, adhesive duration, release pattern of the active substance, etc.).

Because of the oxidative effect of the SXS adhesives a preferred method is to add antioxidants to such SXS-based cement matrices. One example of a commercially available, suitable antioxidant is Irganox® (by CIBA).

Another example consists in hot-meltable adhesives that are based on ethylene vinyl acetate copolymers ("EVA adhesives"). EVA adhesives of that type are described for instance in U.S. Pat. No. 4,144,317. EVA adhesives offer good adhesive properties, they are easy to produce and process and are well tolerated on the skin. They are available for instance from Beardow Adams (13/BA).

It was possible both with hot-meltable SXS-type adhesives and with hot-meltable EVA-type adhesives to produce rotigotine-containing TTSs that encompassed hot-melt cement matrices and released the rotigotine in proper amounts (FIG. 7).

FIG. 9 shows the in-vitro permeation, through murine skin, of rotigotine from EVA-based hot-melt TTSs with varying rotigotine contents, produced by fused extrusion in an extruder.

Therefore, one object of this invention is a transdermal therapeutic system (TTS) encompassing a rotigotine-containing cement matrix, characterized in that the cement matrix contains a hot-meltable adhesive in which the active substance, rotigotine ((−)-5,6,7,8-tetrahydro-6-[propyl[2-(2-thienyl)ethyl-)amino]-1-naphthol), is dispersed and partly or completely dissolved, said hot-meltable adhesive being of the SXS-type or EVA-type.

One form of implementation of this invention is thus represented by a hot-melt TTS that comprises a cement matrix containing:

(a) 50-99 weight % of a hot-meltable adhesive, (b) 1-40 weight %, preferably 5-30 weight %, desirably 9-30 weight % and ideally 15-25 weight % rotigotine, and (c) 0-40 weight %, preferably 2-25 weight % and desirably 5-25 weight % of an internal-phase component preferably selected from the group of polysaccharides, substituted polysaccharides, polyethylene oxides, polyvinyl acetates, polyvinyl pyrrolidones with or without softeners, polyethylene glycols, polypropylene glycols, acrylates, copolymers from polyvinyl pyrrolidone and (poly) vinyl acetate, copolymers from ethylene and vinyl acetate, as well as polyvinyl alcohols with a softener such as glycerin, plus 0-10 weight %, preferably 0-5% and most desirably 0-3% of other additives such as tackifiers, antioxidants, stabilizers and/or permeation boosters, with the hot-meltable adhesive (a) preferably selected as (a1) an EVA adhesive, (a2) an SXS adhesive, or (a3) a mixture consisting of (i) 70-99 weight % of an amine-resistant silicone adhesive, and (ii) 1-30 weight %, preferably 3-15 weight % and ideally 4-10 weight % of a suitable softener, preferably an organic wax—most desirably ceresin or ozokerite, where, optionally, softeners may be added to the EVA adhesive (a1) and to the SXS adhesive (a2) and, if an SXS adhesive is used, an antioxidant is added.

If an individually hot-meltable adhesive for instance of the SXS type or of the EVA type is to be adapted to specific processing requirements, it is again possible, as an option, to add other substances to the composition, such as softeners, tackifiers, antioxidants, amphiphilic polymers, etc.

A comparison of the release pattern of rotigotine from the various hot-melt adhesives revealed that the TTS with the silicone-based hot-melt adhesive is the most efficacious. With the SXS-based and EVA-based hot-melt TTS, the rotigotine release drops off to a level that is no longer therapeutically effective at a point where about 30 weight % of the rotigotine is still present in the cement matrix. By contrast, the silicone-based hot-melt TTS allowed nearly total depletion.

Therefore, a rotigotine-containing hot-melt TTS produced with a silicone-based hot-melt adhesive as described above is given particular preference.

EXAMPLES

Comparative Reference Example

Solvent-Based Silicone TTS 1.8 g of (free-base) rotigotine was dissolved in 2.4 g ethanol and added to 0.4 g Kollidon 90 F (dissolved in 1 g ethanol). The resulting mixture was added to a 74% solution of silicone polymers (8.9 g BIO-PSA 7-4201+8.9 g BIO-PSA 7-4301 [Dow Corning]) in heptane. After adding 2.65 g petroleum ether the mixture was agitated for 1 hour at 700 rpm to produce a homogeneous dispersion. After lamination onto polyester it was dried at 50° C. The final weight of the patch was 50 g/cm$^2$.

Example 1

Silicone-Based Hot-Melt TTS with 15% Rotigotine Produced in Lab Quantities (a) Silicone Hot-Melt Adhesive The silicone-based hot-melt cements employed contained the BIO-PSA 7-4300 silicone adhesive (Dow Corning, Michigan) mixed with ozokerite or ceresine softeners at 5%, 10% or 15% of the overall weight of the adhesive mixture (purchased from Dow Corning).

(b) Producing the TTS 8.5 g of a silicone-based adhesive mixture as described in (a) was heated to 160° C. over about 20 minutes until a homogeneous melt was obtained. 1.5 g (free-base) rotigotine was added and the mixture was kept at 160° C. for another 5 minutes. The mixture was then manually homogenized and laminated onto a preheated foil (120° C., gap width 250 μm). 5 cm$^2$ sections were then cut out.

Example 2

Producing a Silicone-Based Hot-Melt TTS with an Internal Phase

This was produced as in Example 1, with 0.5 g of an internal-phase component added together with the rotigotine.

Example 3

Producing a Silicone-Based Hot-Melt TTS in Lab Quantities with Varied Parameters The TTSs were in all cases produced as in Examples 1 and 2, while the different parameters such as the type of wax, the wax content, the concentration of the internal-phase component, the active-substance content and the patch density were varied as follows:

TABLE 1

| Silicone-based Hot-melt TTS | | | | | | |
|---|---|---|---|---|---|---|
| Lot No. | Ceresine Content [% w/w] | Ozokerite Content [% w/w] | Internal Phase Type & Content [% w/w] | Theoret. Rotigotine Content [% w/w] | Actual Rotigotine Content (n = 5) [% w/w] | Weight of Adhesive Matrix (n = 10) [g/m$^2$] |
| 20011031 | 15 | — | PVP/10 | 9 | 8.51 | 108 |
| 20011032 | 15 | — | PVP/2 | 9 | 9.23 | 83 |
| 20011035 | 15 | — | PVP/2 | 15 | 15.81 | 66 |
| 20011036 | 15 | — | PVP/10 | 15 | 15.56 | 100 |
| 20012038 | 15 | — | PVP/2 | 9 | n.d. | 123 |
| 20012040 | 15 | — | PVP/2 | 15 | n.d. | 118 |
| 20012042 | 15 | — | PVP/2 | 25 | n.d. | 114 |
| 20103042 | 15 | — | 0 | 15 | 15.25 | 57 |
| 20103043 | 15 | — | PVP/25 | 15 | 14.04 | 127 |
| 20105038 | 15 | — | 0 | 9 | 8.75 | 91 |
| 20105039 | 15 | — | PVP/2 | 9 | 9.07 | 88 |
| 20105040 | 15 | — | PVP/10 | 9 | 9.14 | 91 |
| 20105041 | 5 | — | 0 | 9 | 8.08 | 106 |
| 20105043 | — | 5 | 0 | 9 | 8.03 | 105 |
| 20105044 | 15 | — | 0 | 15 | 14.50 | 78 |
| 20105045 | 15 | — | 0 | 25 | 25.20 | 77 |
| 20106016 | — | 15 | 0 | 9 | 8.12 | 88 |
| 20107040 | — | 5 | 0 | 15 | 13.71 | 99 |
| 20107041 | — | 5 | 0 | 25 | 24.71 | 84 |
| 20109009 | — | 15 | 0 | 15 | 13.28 | 89 |
| 20109010 | 5 | — | 0 | 15 | 14.09 | 107 |
| 20111059 | — | 5 | 0 | 25 | 73.95 | 54 |
| 20111058 | — | 5 | 0 | 15 | 14.57 | 54 |
| 20111057 | — | 5 | 0 | 9 | 8.64 | 56 |
| 20109043 | — | 5 | 0 | 25 | 22.69 | 117 |
| 20105044 | — | 15 | 0 | 15 | 14.49 | 57 |
| 20103043 | — | 15 | 0 | 15 | 14.04 | 78 |
| WE11682*) | — | — | PVP/2 | 9 | 8.83 | 50 |
| 20107011*) | — | — | PVP/2 | 9 | 9.90 | 110 |

*)Solvent-based comparative reference example;
PVP = polyvinyl pyrrolidone

The rotigotine content and the weight of the cement matrix were determined as follows: 10 patches sized 5 cm$^2$, 10 cm$^2$ or 20 cm$^2$ were punched out and individually weighed, and the weight was corrected by subtracting the average weight of the blank foils (measured by weighing sections of the same size, i.e. 5, 10 or 20 cm$^2$, respectively).

Example 4

Producing SXS- or EVA-Based Hot-Melt TTS in Lab Quantities 8.5 g of the SXS hot-melt adhesive (Duro-Tak 34-4230 by National Starch & Chemical) or 8.5 g of the EVA hot-melt adhesive was heated at 160° C. for about 20 minutes until a homogeneous melt was obtained. 1.5 g or, respectively, 1.65 g of rotigotine base was added and the mixture was manually homogenized. The mixture was then laminated onto a preheated chill roll (120° C.). 5 cm$^2$ patches (for permeation experiments) and 20 cm$^2$ patches (for determining the patch weight) were then cut out. The matrix weight is shown in Table 2 below:

TABLE 2

| Lot No. | Adhesive | Internal-Phase Content [% w/w] | Theoretical Active-Substance Content [% w/w] | Actual Active-Substance Content [% w/w] | Weight (n = 10) [g/m$^2$] | Purity % (220 nm/272 nm) |
|---|---|---|---|---|---|---|
| 20103041 | SXS | — | 15 | 14.96 | 85 | 94.9/94.3 |
| 20103048 | EVA | — | 16.2 | 18.24 | 58 | 98.1/99.7 |
| 20103047 | EVA | — | 16.2 | 15.96 | 127 | 98.8/99.9 |

Example 5

Producing a Silicone-Based Hot-Melt TTS with 15% Rotigotine and 5% Internal Phase in an Extruder A. Producing a Premelt of the Silicone-Adhesive Mixture The desired amount of the silicone-adhesive mixture as described in Example 1 was preheated to 140° C. and placed in a metering unit (Meltex GR 12-1 by Melzer). The mixture was then volumetrically metered into the extruder.

B. Producing the Cement Matrix by the Hot-Melt Method

A dual-screw extruder (25×24D by Dr. Collin GmbH) was used for small to moderate production quantities and a dual-screw extruder (ZSK25 by Werner Pfleiderer, Stuttgart) was used for large production quantities. The process conditions were 5 kg/h, with 120-140° C. heat zones. A Melzer CL200 was used for the laminating.

Example 6

Producing a Silicone-Based Hot-Melt TTS in the Extruder with Varied Parameters The TTS was in all cases produced as described in Example 5, with the parameters varied as follows:

TABLE 3

| No. | Lot No. | Scale | Static Mixing | Ceresine Content [% w/w] | Internal Phase Type & Content [% w/w] | Theoret. Rotigotine Content [% w/w] | Actual Rotigotine Content (n = 5) [% w/w] | Matrix Weight (n = 10) [g/m²] | Rotigotine Purity [%] (220 nm/272nm) |
|---|---|---|---|---|---|---|---|---|---|
| 1 | 20105025 | large | − | 15 | PVA/10 | 9 | 3.88 | 117 | 99.3/99.7 |
| 2 | 20105025 | large | + | 15 | PVA/10 | 9 | 7.16*) | 117 | 99.3/99.9 |
| 3 | 20105018 | large | − | 15 | PVA/10 | 9 | 9.16 | 92 | 99.4/100 |
| 4 | 20105018 | large | + | 15 | PVA/10 | 9 | 8.36 | 86 | 99.5/100 |
| 5 | 20109006 | small | − | 15 | PVA/10 | 9 | 8.80 | 82 | 99.6 |
| 6 | 20109007 | small | − | 15 | PVPVA/10 | 9 | 3.96 | 98 | 98.3 |
| 7 | 20109008 | small | − | 15 | PEO/10 | 9 | 7.28 | 88 | 99.1 |
| 8 | 20108030 | small | + | 15 | — | 25 | 22.43 | 187 | 99.2/n.d. |
| 9 | 20105045 | small | − | 15 | — | 25 | 25.1 | 77 | 98.7/96.9 |

PVA = polyvinyl acetate;
PEO = polyethylene oxide
PVPVA = polyvinyl pyrrolidone-vinyl acetate copolymer

Example 7

Producing EVA-Based Hot-Melt TTS in an Extruder

All TTSs were produced as described in Example 5, with the TTSs having the following compositions:

TABLE 4

| Lot No. | Scale | Internal-Phase Content [% w/w] | Theoretical Active-Substance Content [% w/w] | Actual Active-Substance Content (n = 5) [% w/w] | Weight (n = 10) [g/m²] | Rotigotine Purity [%] (220 nm/272 nm |
|---|---|---|---|---|---|---|
| 20103048 | small | — | 16.2 | 18.24 | 58 | 98.1/99.7 |
| 20103047 | small | — | 16.2 | 15.96 | 12.7 | 98.8/99.9 |
| 20109019 | large | — | 9 | 8.62 | 93 | 98.9/99.9 |
| 20109045 | large | — | 15 | 15.08 | 104 | 99.4/n.d. |
| 20109020 | large | — | 20 | 18.57 | 89 | 96.1/n.d. |

Example 8

Determining the Flux of the Active Substance in the Murine-Skin Model

For measuring the flux through murine skin, abdominal and dorsal skin about 120 to 150 μm thick was used. A punched-out TTS with a surface area of 2.55 $cm^2$ in a horizontal diffusion cell was fastened to the keratic side of the abdominal and dorsal skin of hairless mice. Immediately thereafter the acceptor chamber of the cell was filled with a phosphate buffer solution (0.066 molar) preheated to 32° C., with a pH 6.2 and bubble-free, and the release medium was thermostatically controlled at 32±0.5° C.

At the time of the sampling the release medium was replaced with fresh medium thermostatically controlled at 32±0.5° C. The rotigotine release was determined by HPLC as described in Example 10.

Example 9

Determining the Rotigotine Flux in the Human-Skin Model

The Rotigotine flux through human skin was essentially determined as described by H. Tanojo et al. in J. Control Rel. 45 (1997) 41-47.

For that purpose, human skin about 250 μm thick was harvested from an abdomen. A TTS with a surface area of 2.545 $cm^2$ was applied on an identical area of the human skin, with the skin on the acceptor side resting on a silicone membrane (FIG. 11). The acceptor phase used was PBS (0.066 molar) at pH 6.2 and a temperature of 32±0.5° C. The experiments were conducted with a flux of 5 mL/h over 72 hours, with samples taken every 3 hours. At the time of the sampling the release medium was replaced with fresh medium thermostatically controlled at 32±0.5° C. and the amount of the released rotigotine was measured by HPLC. The flux rate Q(t) relative to the surface of the measuring cell (0.552 $cm^2$) was determined using this formula:

$Q(t)$=μg/$cm^2$=rotigotine concentration acceptor volume divided by 0.552 $cm^2$ Example 10

Rotigotine Analytics (a) Analytics of the Active-Substance Release

The flux of the active substance through the skin preparations was measured by HPLC (RPC18 LichroCART 75-4 Supersphere 60 select column) under the following conditions: 650 parts by volume (VP) water, 350 VP acetonitrile, 0.5 VP methane sulfonic acid; room temperature; wavelength: 272 nm; flux 2 ml.

(b) Analytics of the Active Substance in the Matrix (b1) Preparing the Matrix

The cement matrix was mixed with 0.1% methane sulfonic acid, agitated, centrifuged and measured.

(b2) Analytics of the Active-Substance Content

The active-substance content was determined by isocratic HPLC under the following conditions:

Solubilizer: 65 volume parts water with 0.05% methane sulfonic acid; 35 volume parts acetonitrile with 0.05% methane sulfonic acid.

Column: LiChroCART 75×4 mm, Supersphere 60 RP-select B 5 μm.

Flow rate: 2 mL/min, column temperature: 30° C.

UV detection (272 nm).

(b3) Analytics of the Active-Substance Stability:

The purity of rotigotine was determined by the gradient HPLC method with an aqueous and an organic (acetonitrile) phase, each with 0.05% methane sulfonic acid added. The organic component rose from the initial 5% to 60% over 35 minutes.

Column: LiChrosphere 100 CN, 125 mm×4.6 mm, 5 μm.

Flow rate: 1.0 mL, column temperature: 40° C.

UV detection (2 wavelengths: 272 and 220 nm).

(b4) Determining the Dynamic Viscosity

The dynamic viscosity was determined as described in U.S. Pat. RE 36,754.

The invention claimed is:

1. A transdermal therapeutic system (TTS) comprising an active-substance-containing cement matrix, wherein the cement matrix comprises a hot-meltable adhesive in which the active substance is dispersed and melted using a hot-melt process, and wherein the active substance is rotigotine and is partly or completely dissolved in the adhesive; and wherein the hot-melt process comprises melting and homogenizing components of the cement matrix and rotigotine without solvent in an extruder at a temperature between 120° C. and 160° C. prior to lamination of the cement matrix.

2. The TTS of claim 1, wherein the hot-meltable adhesive comprises an amine-resistant silicone adhesive and, in mixture therewith, at least one pharmaceutically acceptable softener.

3. The TTS of claim 2, wherein the at least one softener is an organic wax.

4. The TTS of claim 2, wherein the at least one softener is ceresine or ozokerite.

5. The TTS of claim 1, wherein the cement matrix comprises 4-40 weight % rotigotine.

6. The TTS of claim 1, wherein the cement matrix comprises 9-30 weight % rotigotine.

7. The TTS of claim 1, wherein the cement matrix comprises 20-40 weight % rotigotine.

8. The TTS of claim 1, wherein the rotigotine is present in free-base form.

9. The TTS of claim 1, wherein the active-substance-containing cement matrix further comprises an internal-phase component selected from the group consisting of (a) hydrophilic and amphiphilic polymers and mixtures thereof with pharmaceutically acceptable softeners, (b) hydrophilic and amphiphilic copolymers and mixtures thereof with pharmaceutically acceptable softeners, (c) condensates of glycerin and fatty acids, (d) condensates of glycerin and polyols, and (e) mixtures of components (a)-(d).

10. The TTS of claim 1, wherein the active-substance-containing cement matrix further comprises at least one internal-phase component selected from the group consisting of polysaccharides, substituted polysaccharides, polyethylene oxides, polyvinyl acetates, polyvinyl pyrrolidones, copolymers of polyvinyl pyrrolidone and polyvinyl acetate, polyethylene glycol, polypropylene glycol, copolymers of ethylene and vinyl acetate, glycerin-fatty acid esters and mixtures of polyvinyl alcohol with glycerin.

11. The TTS of claim 1, wherein the cement matrix comprises (a) 50-99 weight % of a hot-meltable adhesive, (b) 4-40 weight % of rotigotine, (c) 0-40 weight % of an internal-phase component, and (d) 0-10 weight % of other adjuvants.

12. The TTS of claim 11, wherein the hot-meltable adhesive is an EVA adhesive, an SXS adhesive, or a mixture of (i) 70-99 weight % of an amine-resistant silicone adhesive and (ii) 1-30 weight % of a pharmaceutically acceptable softener.

13. The TTS of claim 11, wherein the rotigotine is present in an amount effective, upon application of the TTS on skin of a human patient, to induce an average plasma concentration of 0.4 to 2 ng/ml rotigotine in the patient for a period of at least 5 days following said application.

14. The TTS of claim 13, wherein the rotigotine is present in an amount effective to induce an average plasma concentration of 0.4 to 2 ng/ml rotigotine in the patient for a period of at least 7 days following said application.

15. The TTS of claim 1, wherein the rotigotine is present in an amount effective, upon application of the TTS on skin of a human patient, to provide transport of rotigotine through the skin at a steady-state flux rate of 200-300 μg per hour.

16. A method for preparing a TTS that comprises a rotigotine-containing cement matrix, the method comprising:

melting and homogenizing components of the cement matrix and rotigotine without solvent in an extruder at a temperature between 120° C. and 160° C. prior to lamination of the cement matrix.

17. The method of claim 16, wherein the method is a two-step method comprising:

melting and homogenizing components of the cement matrix other than rotigotine without solvent, and introducing rotigotine at a temperature between 120° C. and 160° C., into the melted cement matrix.

18. The method of claim 17, wherein the rotigotine is introduced in solid state into the melted cement matrix.

19. The method of claim 17, wherein the rotigotine in the cement matrix has a purity level of at least 98% as measured by HPLC at 220 nm and 272 nm.

20. The TTS of claim 1, wherein the rotigotine is present in a therapeutically effective amount for treatment of a disease associated with a dopamine-metabolism disorder in a human patient, by application of the TTS on skin of the patient.

21. The TTS of claim 20, wherein the disease associated with a dopamine-metabolism disorder is Parkinson's disease.

22. The TTS of claim 20, wherein the disease associated with a dopamine-metabolism disorder is restless leg syndrome.

23. A method for treating a disease associated with a dopamine-metabolism disorder in a human patient, comprising applying to skin of the patient a TTS of claim 1 in a therapeutically effective amount.

24. The method of claim 23, wherein the disease associated with a dopamine-metabolism disorder is Parkinson's disease.

25. The method of claim 23, wherein the disease associated with a dopamine-metabolism disorder is restless leg syndrome.

* * * * *

UNITED STATES PATENT AND TRADEMARK OFFICE

CERTIFICATE OF CORRECTION

PATENT NO. : 8,211,462 B2
APPLICATION NO. : 10/630633
DATED : July 3, 2012
INVENTOR(S) : Armin Breitenbach and Hans-Michael Wolff It is certified that error appears in the above-identified patent and that said Letters Patent is hereby corrected as shown below:

In the Specification

Column 5, line 44, replace “the most 150 Pa,” with -- the most 150 Pa.s, --.

Column 5, line 45, replace “more than 120 Pa, desirably less than 100 Pa and” with -- more than 120 Pa.s, desirably less than 100 Pa.s and --.

Column 5, line 46, replace “even 60 Pa.” with -- even 60 Pa.s. --.

Column 5, line 51, replace “than 150 Pa.” with -- than 150 Pa.s. --.

Column 6, line 7, replace “over 150 Pa to below 50 Pa.” with -- over 150 Pa.s to below 50 Pa.s. --.

Column 8, line 46, replace “singlµµe” with -- single --.

Column 8, line 19, replace “µM” with -- µm --.

Column 8, line 20, replace “µM” with -- µm --.

Column 9, line 21, replace “more than 150 Pa,” with -- more than 150 Pa.s, --.

Column 9, line 22, replace “than 120 Pa and most desirably less than 80 Pa.” with -- than 120 Pa.s and most desirably less than 80 Pa.s. --.

Column 17, Table 1, Column Actual Rotigotine Content, Lot No. 20111059, replace “73.95” with -- 23.95 --.

Column 19, Table 3, Column Actual Rotigotine Content, No. 6, replace “3.96” with -- 8.96 --.

Signed and Sealed this
Twelfth Day of November, 2013

Teresa Stanek Rea
*Deputy Director of the United States Patent and Trademark Office*

Column 19, Table 3, Column Actual Rotigotine Content, No. 9, replace “25.1” with -- 25.2 --.

Column 19, Table 4, Column Weight, Lot No. 20103047, replace “12.7” with -- 127 --.